United States Patent
Iles et al.

(10) Patent No.: US 12,044,685 B2
(45) Date of Patent: Jul. 23, 2024

(54) VIRUS AND EXOSOME SAMPLE PREPARATION AND ANALYSIS METHODS

(71) Applicant: PPR SCIENCES LIMITED, Dublin (IE)

(72) Inventors: Raymond Kruse Iles, Norfolk (GB); Jason Kruse Iles, Ely (GB)

(73) Assignee: PPR SCIENCES LIMITED, Dublin (IE)

( * ) Notice: Subject to any disclaimer, the term of this patent is extended or adjusted under 35 U.S.C. 154(b) by 54 days.

(21) Appl. No.: 17/320,624

(22) Filed: May 14, 2021

(65) Prior Publication Data
US 2021/0356475 A1 Nov. 18, 2021

Related U.S. Application Data

(60) Provisional application No. 63/025,360, filed on May 15, 2020.

(30) Foreign Application Priority Data

May 15, 2020 (GB) .................................. 2007246

(51) Int. Cl.
*G01N 1/40* (2006.01)
*G01N 33/68* (2006.01)

(52) U.S. Cl.
CPC ....... *G01N 33/6851* (2013.01); *G01N 1/4055* (2013.01); *G01N 2333/005* (2013.01)

(58) Field of Classification Search
CPC ............. G01N 33/6851; G01N 1/4055; G01N 2333/005
See application file for complete search history.

(56) References Cited

PUBLICATIONS

Serafim, V. et al. "Rapid Identification of *E. coli* Bacteriophages using Mass Spectrometry," J Proteomics Enzymol 2017, 6:1, 5 pages (Year: 2017).*
Chavan, R. et al. "Differential proteomic analysis of respiratory samples from patients suffering from influenza," Virus Dis. (Jul.-Sep. 2016) 27(3):226-233 (Year: 2016).*
Blanc, J.-F et al. "Proteomic analysis of differentially expressed proteins in hepatocellular carcinoma developed in patients with chronic viral hepatitis C," Proteomics 2005, 5, 3778-3789 (Year: 2005).*
Fang, C. et al. "Proteome analysis of human liver carcinoma Huh7 cells harboring hepatitis C virus subgenomic replicon," Proteomics 2006, 6, 519-527 (Year: 2006).*

(Continued)

*Primary Examiner* — Jennifer Wecker
*Assistant Examiner* — Michelle Adams
(74) *Attorney, Agent, or Firm* — Jordan IP Law, LLC

(57) ABSTRACT

Provided are methods for preparing a biological sample for analysis for the presence of a virus, or an exosome or other extra-cellular vesicle, by matrix assisted laser desorption ionisation time of flight mass spectrometry (MALDI-ToF MS). The preparation involves mixing the sample with at least one cationic viral envelope/vesicle disruptor compound, or at least one disulphide reducing agent, or a combination thereof; and at least one mass spectrometry grade solvent. Also provided are methods for analysing a biological sample for the presence of a virus, or an exosome or other extra-cellular vesicle, using MALDI-ToF MS once prepared.

17 Claims, 16 Drawing Sheets

(56) References Cited

PUBLICATIONS

Luo, H. et al. "Identification of plant viruses using one-dimensional gel electrophoresis and peptide mass fingerprints," Journal of Virological Methods 165 (2010) 297-301 (Year: 2010).*

Bardell, D., "Effect of Acetone Fixation on Infectivity and Antigenicity of Respiratory Syncytial Virus and Adenovirus in the Fluorescent Antibody Test", *Journal of Clinical Microbiology*, pp. 157-160, Feb. 1975.

Ihling, C. et al., "Mass Spectrometric Identification of SARS-CoV-2 Proteins from Gargle Solution Samples of COVID-19 Patients", *Journal of Proteome Research*, Apr. 2020, bioRxiv preprint.

Kariwa et al., "Inactivation of SARS coronavirus by means of povidone-iodine, physical conditions, and chemical reagents", *Japanese Journal of Veterinary Research*, vol. 52, No. 3, pp. 105-112, 2004.

Lin et al., "Proteome Profiling of Urinary Exosomes Identifies Alpha 1-Antitrypsin and H2B1K as Diagnostic and Prognostic Biomarkers for Urothelial Carcinoma", Scientific Reports, 6:34446, Sep. 2016.

Medrum, O.W. et al., "Mucin gel assembly is controlled by a collective action of non-mucin proteins, disulfide bridges, $Ca^{2+}$-mediated links, and hydrogen bonding", Sci Rep 8, 5802, Apr. 2018.

Zhu et al., "MALDI Detection of Exosomes: A Potential Tool for Cancer Studies", Chem 5., pp. 1318-1336, May 2019.

Calderaro et al., Identification of different respiratory viruses, after a cell culture step, by matrix assisted laser desorption/ionization time of flight mass spectrometry (MALDI_TOF MS), *Sci Rep 6*, vol. 36082, 2016.

Cobo, "Application of MALDI_TOF Mass Spectrometry in Clinical Virology: A Review", *The Open Virology Journal*, vol. 7, pp. 84-90, 2013.

"Detergents for Cell Lysis and Protein Extraction: ThermoFisher Scientific".

Dillon et al., "Quantitative proteomic analysis in HCV-induced HCC reveals sets of proteins with potential significance for racial disparity", *Journal of Translational Medicine*, vol. 11, No. 239, 2013.

Iles et al., "Development of a Clinical MALDI-ToF Mass Spectrometry Assay for SARS-CoV-2: Rational Design and Multi-Disciplinary Team Work", *Diagnostics*, vol. 10. pp. 746, 2020.

Iles et al., "Direct MALDI-ToF mass spectrometry, detection of SARS-1 and SARS-2 (COVID-19) fusion glycol-peptide ejected from Spike proteins", *Proceedings of the 68th ASMS Conference on Mass Spectrometry and Allied Topics*, 2020.

Jang et al., Enhanced Reliability of Avian Influenza Virus (AIV) and Newcastle Disease Virus (NDV) Identification Using Matrix-Assisted Later Desorption/Ionization-Mass Spectrometry (MALDI-MS), *Anal. Chem.*, vol. 83, pp. 1717-1725, 2011.

LC MS Grade Water (≥99.9%)-4x4L, PerkinElmer, Accessed Sep. 15, 2023. https://www.perkinelmer.com/product/water-lc-ms-grade-case-4x4l-n9304940.

Sigma-Aldrich, Water—for UHPLC, for mass spectrometry # 900682. CAS # 7732-18-5, Accessed Sep. 15, 2023. www.sigmaaldrich.com.

Sigma-Aldrich, Water—Acetonitrile with 0.1% ammonium acetate tested for UHPLC-MS # 14274. CAS # 148642-19-7, Accessed Sep. 15, 2023. www.sigmaaldrich.com.

Solvents for LC-MS | Thermo Fisher Scientific—US, Accessed Sep. 15, 2023. https://www.thermofisher.com/uk/en/home/life-science/protein-biology/protein-mass-spectrometry-analysis/calibration-solutions-standards-solvents-mass-spectrometry/solvents-lc-ms.html.

Water, LC-MS grade LC-MS, for liquid chromatography, Accessed Sep. 15, 2023. https://www.chem-lab.be/en-gb/prod/1400165/Water-LC-MS-grade.

* cited by examiner

VIRUS AND EXOSOME SAMPLE PREPARATION AND ANALYSIS METHODS

CROSS-REFERENCE TO RELATED APPLICATIONS

This application claims the benefit of U.S. Provisional Application No. 63/025,360, which was filed on May 15, 2020, and Great Britain Application No. 2007246.8, which was filed on May 15, 2020. The entire contents of these applications are incorporated herein by reference.

FIELD OF THE INVENTION

This invention relates to methods for preparing a biological sample for analysis for the presence of a virus, or an exosome or other extra-cellular vesicle, by matrix assisted laser desorption ionisation time of flight mass spectrometry (MALDI-ToF MS). This invention also relates to methods for analysing a biological sample for the presence of a virus, or an exosome or other extra-cellular vesicle, using MALDI-ToF MS, wherein the biological sample has first been processed using a method of the invention. The methods of the invention may be applied to assist diagnosis of viral infections in patients or to identify useful biomarkers.

BACKGROUND OF THE INVENTION

Mass spectrometry can be used to detect and identify markers originating from virus particles, in particular viral envelope groups or fragments thereof, by virtue of their characteristic peaks and peak patterns generated in mass spectra.

There remains a need for methods for processing biological samples from patients suspected of having a viral infection for MALDI-ToF analysis so that diagnostic virus-originating marker peaks and peak patterns in MALDI-ToF spectra are not obscured by conditions and factors introduced by the sample processing procedure. An advantage of MALDI-ToF MS over other types of mass spectrometry is that the process of soft-ionization causes little or no fragmentation of analytes, allowing the molecular ions of large molecules to be identified even within mixtures.

The methods of this invention address this need and enable sensitive and reliable detection of virus-originating markers by MALDI-ToF MS. The methods therefore provide a cost effective and rapid means of screening large numbers of samples and/or diagnosing viral infections, such as infections by influenza viruses or SARS-CoV-2 (COVID-19).

Ihling et al. "MS Analysis of SARS-CoV-2 Proteins from Gargle Solutions", COVID-19 SARS-CoV-2 preprints from medRxiv and bioRxiv, posted 19 Apr. 2020 (doi: https://doi.org/10.1101/2020.04.18.047878) discloses a method for detection of unique peptides originating from SARS-CoV-2 nucleoprotein by liquid chromatography mass spectrometry (LC/MS) using nano-electrospray ionisation. The disclosed sample preparation procedure involves mixing gargle solutions from COVID-19 patients with acetone (−20° C.). The mixture is stored overnight at −20° C. and then centrifuged to provide a precipitate in the form of the pellet. The pellet is then dissolved in SMART™ Digest buffer (Thermofisher) and heated to 75° C. for 10 minutes. The solution is then treated with PNGase F, trypsin in further SMART™ Digest buffer, dithiothreitol and iodoacetamide to provide the sample for LC/MS analysis. No MALDI-ToF mass spectrometry analysis was conducted and the peptides detected were of significantly lower molecular weight than the majority of markers detectible using the methods of the present invention. The SMART™ Digest buffer comprises inorganic salts including $CaCl_2$. The inorganic salts may prevent efficient ionisation of virus-originating markers in MALDI by charge generated from the MALDI matrix material when the matrix material absorbs laser energy. The inorganic salts may also reduce detector sensitivity over time. The sample prepared in Ihling et al. is therefore not suitable for MALDI-ToF analysis.

Exosomes are membrane-bound extracellular vesicles that are produced in the endosomal compartment of most eukaryotic cells. They contain constituents such as proteins, DNA and RNA from the cells that secrete them, held within a lipid membrane. They may be found in bodily fluids including blood, urine and cerebrospinal fluid and have also been identified within the intercellular tissue matrix.

Extracellular vesicles including exosomes carry markers of the cells from which they originate and have specialised functions in physiological processes, from coagulation and intercellular signalling to waste management. For example, intercellular communication through exosomes may be involved in the pathogenesis of various disorders, including cancer, neurodegeneration and inflammatory diseases. Exosomes can also be engineered to deliver therapeutic payloads, including short interfering RNAs, antisense oligonucleotides, chemotherapeutic agents and immune modulators.

There is a growing interest in clinical applications of extra-vesicular particles and exosomes as biomarkers. The detection and identification of exosomes and other extracellular vesicles in bodily fluids may therefore be of assistance in the diagnosis of certain conditions and in monitoring of the treatment or progression of diseases.

Mass spectrometry can be used to detect and identify biomarkers originating from exosomes and other extracellular vesicles by virtue of their characteristic peaks and peak patterns generated in mass spectra. Zhu at al have reported use of MALDI-ToF mass spectrometry to analyse intact exosomes isolated from serum-free cell culture supernatant (Chem 5, 1318-1336, May 9, 2019). Lin et al have utilised MALDI-ToF mass spectrometry to analyse protein biomarkers for urothelial carcinoma extracted from exosomes (Scientific Reports|6:34446|DOI: 10.1038/srep34446, 30 Sep. 2016). The exosomes were treated with formic acid or a mixture of formic acid and acetonitrile to extract the proteins. Use of an RIPA lysis buffer containing 10 mM Tris-HCl, 1 mM ethylenediaminetetraacetic acid, 1 mM ethylene glycol tetraacetic acid, 50 mM NaCl, 50 mM NaF, 20 mM $Na_4P_2O_7$, 1 mM $Na_3VO_4$, and 1% Triton X-100 to extract proteins was also investigated but resulted in the MALDI-TOF signals being significantly impaired, even though the sample was purified before MALDI-TOF analysis.

There remains a need for alternative methods for processing biological samples for MALDI-ToF analysis so extracellular vesicle (including exosome)-originating marker peaks and peak patterns in MALDI-ToF spectra are not obscured by conditions and factors introduced by the sample processing procedure.

The methods of this invention address this need and enable sensitive and reliable detection of extracellular vesicle (including exosome)-originating markers by MALDI-ToF MS. The methods therefore provide a cost effective and rapid means of screening large numbers of samples for the presence of specific biomarkers derived from extracellular vesicles including exosomes.

SUMMARY OF THE INVENTION

In a first aspect, the invention is directed to a method (referred to herein as "processing method B") for preparing a biological sample for analysis for the presence of an enveloped virus, or an exosome or other extra-cellular vesicle, by MALDI-ToF mass spectrometry, the method comprising mixing the sample with:
  i. at least one cationic viral envelope/vesicle disruptor compound, or at least one disulphide reducing agent, or a combination thereof; and
  ii. at least one mass spectrometry grade solvent.

In a second aspect, the invention is directed to a method for analysing a biological sample for the presence of an enveloped virus, or an exosome or other extra-cellular vesicle, the method comprising:
  a) mixing the sample with:
    i. at least one cationic viral envelope/vesicle disruptor compound, or at least one disulphide reducing agent, or a combination thereof; and
    ii. at least one mass spectrometry grade solvent; and
  b) subjecting the resulting mixture to MALDI-ToF mass spectrometric analysis.

In a third aspect, the invention is directed to a method (referred to herein as "processing method A") for preparing a biological sample for analysis for the presence of a virus, or an exosome or other extra-cellular vesicle, by MALDI-ToF mass spectrometry, the method comprising:
  (i) treating the sample at a temperature of from 2 to 10° C. (preferably 2 to 8° C., more preferably from 3 to 8° C., most preferably from 4 to 6° C.) with a volatile organic solvent to form a precipitate comprising any virions, exosomes or other extra-cellular vesicles, present in the sample; and
  (ii) separating the precipitate from the supernatant and retaining the precipitate for analysis.

In a fourth aspect, the invention is directed to a method for analysing a biological sample for the presence of a virus, or an exosome or other extra-cellular vesicle, the method comprising:
  (i) treating the sample at a temperature of from −25° C. to 18° C. (preferably 2 to 10° C., more preferably from 3 to 8° C., most preferably from 4 to 6° C.), with a volatile organic solvent to form a precipitate comprising any virions, exosomes or other extra-cellular vesicles present in the sample;
  (ii) separating the precipitate from the supernatant;
  (iii) dissolving or suspending the precipitate in a mass spectrometry grade solvent; and
  (iv) subjecting the solution or dispersion to MALDI-ToF mass spectrometric analysis.

Processing methods A and B may preferably be combined. Thus, in a fifth aspect, the invention is directed to a method (referred to herein as "processing method C") for preparing a biological sample for analysis for the presence of an enveloped virus, or an exosome or other extra-cellular vesicle, by MALDI-ToF mass spectrometry
  (a) treating the sample at a temperature of from −25° C. to 18° C. (preferably 2 to 10° C., more preferably from 3 to 8° C., most preferably from 4 to 6° C.) with a volatile organic solvent to form a precipitate comprising any virions, exosomes or other extra-cellular vesicles present in the sample;
  (b) separating the precipitate from the supernatant;
  c) mixing the precipitate with:
    i. at least one cationic viral envelope/vesicle disruptor compound, or at least one disulphide reducing agent, or a combination thereof; and
    ii. at least one mass spectrometry grade solvent.

In a further aspect, the invention is directed to a method for analysing a biological sample for the presence of an enveloped virus, or an exosome or other extra-cellular vesicle, the method comprising:
  (a) treating the sample at a temperature of from −25° C. to 18° C. (preferably 2 to 10° C., more preferably from 3 to 8° C., most preferably from 4 to 6° C.) with a volatile organic solvent to form a precipitate comprising any virions present in the sample;
  (b) separating the precipitate from the supernatant;
  (c) mixing the precipitate with:
    i. at least one cationic viral envelope/vesicle disruptor compound, or at least one disulphide reducing agent, or a combination thereof; and
    ii. at least one mass spectrometry grade solvent; and
  (d) subjecting the resulting mixture to MALDI-ToF mass spectrometric analysis.

The above methods are preferably used for the analysis of biological samples for the presence of a virus.

In a further aspect, the present invention provides a method of diagnosing a viral illness in a patient, the method comprising subjecting a sample from the patient to one of the above analysis methods and reviewing the resulting spectra for one of more peaks indicative of the presence of a virus in the sample.

In a further aspect, the present invention provides a method of screening a patient for a viral illness, the method comprising subjecting a sample from the patient to one of the above analysis methods and reviewing the resulting spectra for the presence or absence of one of more peaks indicative of the presence of a virus in the sample.

In a further aspect, the present invention provides a method of diagnosing an illness or condition in a patient, the method comprising subjecting a sample from the patient to one of the above analysis methods and reviewing the resulting spectra for one of more peaks indicative of the presence of a diagnostic biomarker from an exosome or other extra-cellular vesicle in the sample.

As used herein, a "diagnostic biomarker" refers to a protein or other compound, preferably a protein, derived from an exosome or other extracellular vesicle which is indicative of the presence or absence of a disease. For example, cancerous cells may produce highly specific protein biomarkers. Analysing exosomes or other extracellular vesicle present in bodily fluids for such biomarkers may provide a convenient way to diagnose cancer or to monitor the progress of cancer therapy without the need for invasive tumour biopsies.

In a further aspect, the present invention provides a method of screening a patient for an illness or condition, the method comprising subjecting a sample from the patient to one of the above analysis methods and reviewing the resulting spectra for the presence or absence of one of more peaks indicative of the presence of a diagnostic biomarker in the sample.

In the above methods, the volatile organic solvent is preferably acetone.

In the methods of the invention, the reagents used to treat the sample (such as the volatile organic solvent, the at least one cationic disruptor compound, the at least one disulphide reducing agent and/or the at least one mass spectrometry grade solvent) are preferably substantially free, and more preferably completely free, of inorganic salts. For example, any reagents may comprise less than 0.01 mol/L of inorganic salts.

In the methods of the invention, the sample is preferably not treated with any enzyme(s).

Figure 1:
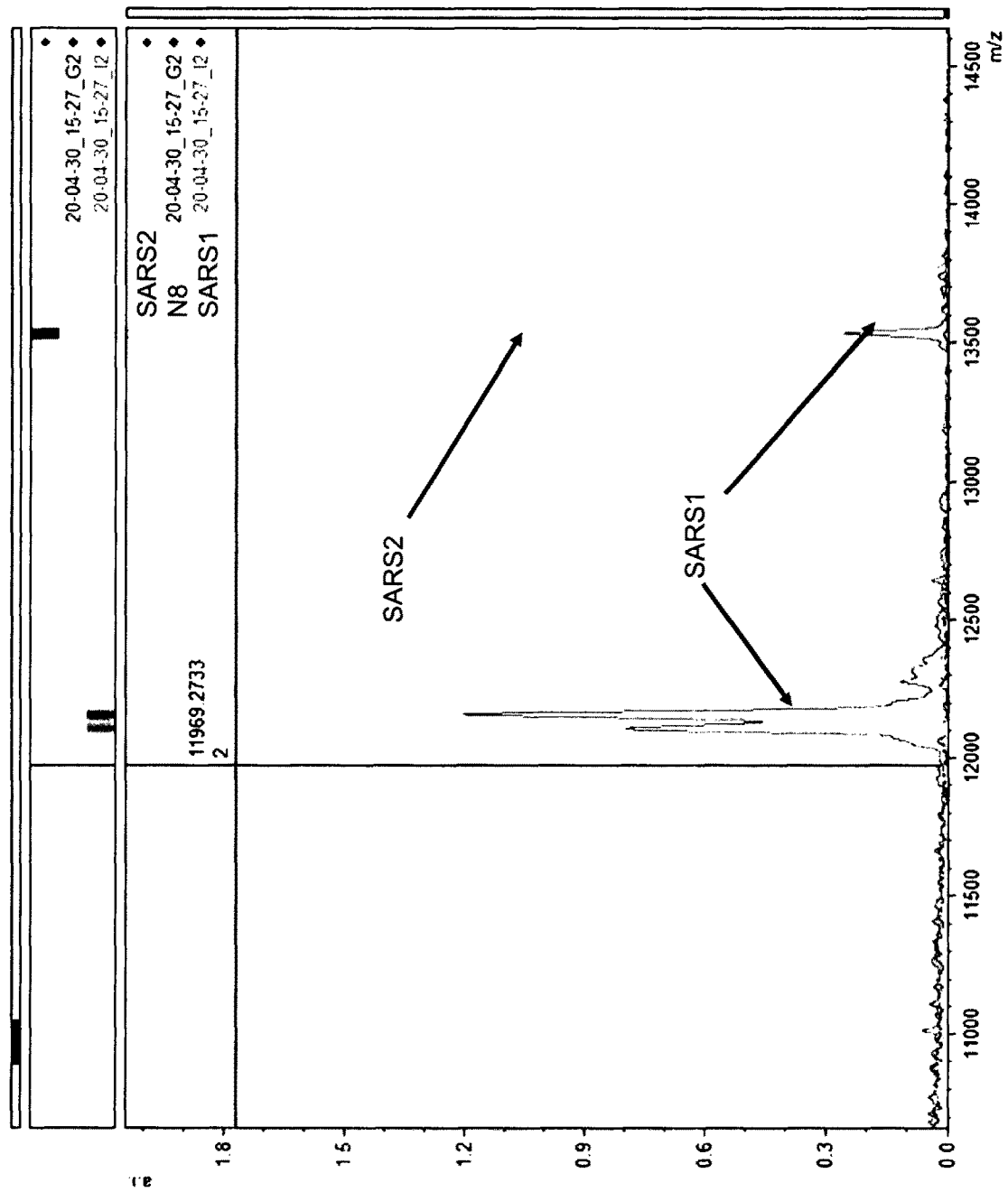
FIG. 1 is a MALDI-ToF mass spectrum showing peaks which are indicative of SARS-CoV-1 (SARS1) and SARS-CoV-2 (SARS2) pseudoviruses.

FIGS. 3 and 4 are MALDI-ToF mass spectra for samples containing live H1N1 influenza virus (Influenza A/England/195/2009) and lymphocytic choriomeningitis virus (LCMV).

FIG. 5 shows a MALDI-ToF mass spectrum for samples containing SARS1 and SARS2 pseudoviruses and a schematic of the spike protein structure.

FIG. 6 shows a MALDI-ToF mass spectrum for samples containing SARS1 and SARS2 pseudoviruses.

FIG. 7 shows a MALDI-ToF mass spectrum for samples containing live Influenza A/Puerto Rico/8/1934 (PR8) virus, Influenza A/England/195/2009 (Swine Flu) and lymphocytic choriomeningitis virus (LCMV).

FIG. 8 shows a MALDI-ToF mass spectrum for samples containing SARS1, SARS2 and N8 influenza pseudoviruses in which the peaks for the three samples overlap.

FIG. 9 shows a MALDI-ToF mass spectrum for samples containing LCMV, Influenza A/Puerto Rico/8/1934 (H1N1 PR8), Influenza A/England/195/2009 (H1N1 Swine Flu), and SARS1, SARS2, and MERS-CoV pseudoviruses.

FIG. 10 is a MALDI-ToF mass spectrum showing a peak at 9200 m/z which is indicative of influenza N9 neuraminidase.

FIG. 11 is a MALDI-ToF mass spectrum showing a peak at 44000 m/z which is indicative of influenza N8 neuraminidase.

FIGS. 12-14 are MALDI-ToF mass spectra for samples containing H1N1 Swine Flu at three m/z ranges (FIG. 12—about 5000 to about 18000, FIG. 13 about 20000 to about 60000, FIG. 14—about 65000 to about 68000).

FIGS. 15 and 16 show results from a study of samples from individuals tested for SARS-CoV-2 using MALDI-ToF mass spectrometry.

DETAILED DESCRIPTION OF THE INVENTION

All preferred features and embodiments herein may be combined in any way. The term "comprising" as used herein also includes the terms "consisting essentially of" and "consisting of".

Biological Samples

The biological samples used in the present invention may be any suitable sample from an individual who might potentially have a viral infection and which could contain virion particles and/or virus-infected cells. The biological samples used in the present invention may also be any suitable sample from an individual which could contain an exosome or other extracellular vesicle. Suitable examples include blood serum, blood plasma, urine, saliva, cerebrospinal fluid, washings from a swab (for example a throat swab), a gargle solution, or a bronchial or lung lavage. Preferably, the biological sample is a swab washing or a gargle solution (particularly for respiratory viruses), optionally wherein the washing solvent is saline or water. Preferably, the individual is a human, and may be a patient suspected of having a viral infection. Preferably, the biological sample contains a candidate virus, exosome or other extracellular vesicle. Prior to treating a sample which may contain a virus with the volatile solvent (as in preparation method A or C1), and/or mixing it with the cationic viral envelope disruptor compound and/or the disulphide reducing agent and the mass spectrometry grade solvent (as in preparation method B or C1), the sample may be mixed into any suitable cell culture media comprising one or more broad spectrum antibiotics and used to inoculate a viral receptive cell line in order to amplify the concentration of any virus that may be present in the sample.

Suitable culture media, antibiotics and cell lines are known in the art and are commercially available. For example, suitable cell culture media include minimum essential medium [MEM]) and suitable broad spectrum antibiotics include penicillin and/or streptomycin. Examples of suitable viral receptive cell lines include Vero C1008 [Vero 76, clone E6, Vero E6] (ECACC 85020206) or human embryo kidney cell lines such as HEK293 [ECACC 85120602]). The inoculated cells may be cultured for 7 to 24 hours, preferably about 12 hours.

The presence of serum (such as fetal bovine serum) in the cell culture media may cause contamination of the sample with proteins from the serum which may ultimately obscure diagnostic virus-originating peaks or peak patterns in the MALDI-ToF spectra. For example, after culturing test samples in cell culture media comprising fetal bovine serum, the inventors have observed peaks at 45,691 m/z (correspond to fetuin) and 33,486 m/z (corresponding to 2+ albumin), even after precipitation as described in preparation method A using acetone as the volatile solvent. Thus, in one preferred embodiment the biological sample is not cultured in a cell culture medium comprising serum. In another preferred embodiment, the biological sample is cultured in a serum-free cell culture medium. In a further preferred embodiment the biological sample is cultured in a culture media comprising serum, wherein the serum is substantially free of MALDI-ToF obscuring serum proteins, such as immunoglobins, haptoglobins, transferrins, albumin and fetuin. However, depending on the candidate virus to be detected, culturing in media comprising serum may still be acceptable provided that the contaminants from the serum do not obscure diagnostic candidate virus-originating peaks or peak patterns in the MALDI-ToF spectra.

After culturing, the culture media is harvested and is then treated or analysed using the methods of the invention. The term "biological sample" as used herein in relation to the methods of the invention therefore includes such harvested culture media.

In a particularly preferred embodiment, the sample that is treated with the viral envelope disruption buffer according to preparation method B is first treated according to preparation method A. In other words, in a preferred aspect, the invention is directed to a method for preparing a biological sample for analysis for the presence of an enveloped virus by MALDI-ToF MS (referred to herein as "preparation method C1") the method comprising:

(a) treating the sample at a temperature of from −25° C. to 18° C. with a volatile organic solvent to form a precipitate comprising any virions present in the sample;

(b) separating the precipitate from the supernatant; and (c) mixing the precipitate with:
   i. at least one cationic viral envelope disruptor compound, or at least one disulphide reducing agent, or a combination thereof; and
   ii. at least one mass spectrometry grade solvent.

In another embodiment, the invention is directed to a method for preparing a biological sample for analysis for the presence of an exosome or other extracellular vesicle by MALDI-ToF MS (referred to herein as "preparation method C2") the method comprising:

(a) treating the sample at a temperature of from −25° C. to 18° C. with a volatile organic solvent to form a precipitate comprising any exosomes or other extracellular vesicles present in the sample;
(b) separating the precipitate from the supernatant; and
(c) mixing the precipitate with:
   iii. at least one cationic vesicle disruptor compound, or at least one disulphide reducing agent, or a combination thereof; and
   iv. at least one mass spectrometry grade solvent.

Embodiments outlined below apply equally to these embodiments, including but not limited to those relating to virus identity, the identity and temperature of volatile solvent, the separation of the precipitate from the supernatant, the cationic viral envelope/vesicle disruptor compounds, disulphide reducing agents, and mass spectrometry grade solvents.

Candidate Viruses

The methods of the invention may enable detection of both enveloped viruses and non-enveloped viruses that may be present in a biological sample by MALDI-ToF MS. The methods are particularly suitable for the detection of enveloped viruses. Enveloped viruses which may be detected using the methods of the invention include any influenza virus, SARS-CoV-1, SARS-CoV-2, MERS-CoV, Lassa virus (LASV), lymphocytic choriomeningitis virus (LCMV), human immunodeficiency viruses (HIV) or Ebola viruses. Suitable influenza viruses include Influenza A viruses (such as H1N1 strains) and Influenza B viruses. Particularly, suitable viruses that may be detected include influenza A viruses, SARS-CoV-1, SARS-CoV-2, MERS-CoV and LCMV.

Cationic Viral Envelope/Vesicle Disruptor Compounds, Disulphide Reducing Agents, Mass Spectrometry Grade Solvents Some of the methods of the invention comprise mixing the biological sample with: (i) at least one cationic viral envelope/vesicle disruptor compound, or at least one disulphide reducing agent, or a combination thereof; and (ii) at least one mass spectrometry grade solvent.

The terms cationic disruptor compound and cationic viral envelope/vesicle disruptor compound are used interchangeably herein.

Preferably, the methods comprise mixing the sample with at least one cationic viral envelope/vesicle disruptor compound, optionally in combination with at least one disulphide reducing agent. References below to a cationic viral envelope disruptor compound apply equally to a cationic vesicle disruptor compound The viral envelope/vesicle disruptor compound(s), the disulphide reducing agent(s) and the mass spectrometry grade solvent(s) may be added to the sample separately or together in any combination. For ease of processing, especially of large numbers of samples, the viral envelope/vesicle disruptor compound(s) and/or the disulphide reducing agent(s) and the mass spectrometry grade solvent(s) are preferably themselves first mixed together to form a solution which is then mixed with the sample(s). The precipitate may be suspended or dissolved in a mass spectrometry grade solvent before the addition of the viral envelope disruptor compound(s) and/or the disulphide reducing agent(s) in additional mass spectrometry grade solvent.

The at least one cationic viral envelope disruptor compound (which term includes cationic detergents and cationic biocides) disrupts the lipid viral envelope membrane and releases/solubilizes virus-originating envelope compounds, including proteins located in the viral envelope, e.g. envelope glycoproteins. Once solubilized these virus-originating envelope compounds or fragments thereof can be detected by MALDI-ToF MS. In particular, solubilized viral envelope proteins or fragments thereof can therefore act as markers of a viral infection.

Similarly, the at least one cationic vesicle disruptor compound disrupts the lipid membrane and releases/solubilizes extracellular vesicle-, including exosome-, originating compounds, including proteins located in the exosome or other vesicle. Once solubilized these extracellular vesicle- or exosome-originating envelope compounds or fragments thereof can be detected by MALDI-ToF MS. In particular, solubilized proteins or fragments thereof can act as markers for the presence of an exosome or other extra-cellular vesicle in the sample.

It is important that the disruptor compounds do not interfere with detection of the diagnostic virus-originating, exosome-originating or extracellular vesicle-originating peaks or peak patterns in the MALDI-ToF spectra. The inventors have found that anionic detergents such as sodium dodecyl sulphate (SDS) swamp the MALDI-ToF detector signal and so prevent identification of such markers, including virus-originating markers. The inventors have also found that the non-ionic detergent tert-octyl-$C_6H_4$—$(OCH_2$-$CH_2)_{9-10}OH$ (Triton X-100; CAS-9002-93-1) is not suitable for preparing a sample for analysis by MALDI-ToF MS.

Preferred for use in the methods of the invention are cationic disruptor compounds which do not readily form micelles at low concentrations, which may interfere with the mass spectra by sequestering virus-originating compounds of interest. If a micelle-forming cationic viral envelope/vesicle disruptor compound is used, it is preferably used a concentration below its critical micelle concentration.

Suitable cationic viral envelope/vesicle disruptor compounds include quaternary ammonium compounds; chlorhexidine gluconate (CHDG); N-(3-aminopropyl)-N-dodecylpropane-1,3-diamine; polyhexamethylene biguanide hydrochloride (PHMB); or a combination thereof, preferably N-(3-aminopropyl)-N-dodecylpropane-1,3-diamine.

N-(3-aminopropyl)-N-dodecylpropane-1,3-diamine is commercially available under the name Lonzabac® 12 from Lonza.

Many quaternary ammonium compounds (quats) which are active as biocides are known in the art and may be used as the cationic disruptor compound according to the present invention. Suitable such compounds include benzalkonium chloride (BAC), benzethonium chloride, methylbenzethonium chloride, cetalkonium chloride, cetylpyridinium chloride, cetrimonium chloride, cetrimonium bromide, cetrimide, tetraethylammonium bromide, dialkyldimethyl ammonium salts such as didecyldimethylammonium chloride, and domiphen bromide. Preferred quaternary ammonium compounds for use in the present invention are didecyldimethyl ammonium chloride (DDAC), and benzalkonium chloride. More preferably, the quaternary ammonium compounds are selected from didecyldimethyl ammonium chloride (DDAC), and benzalkonium chloride.

Particularly suitable are 50% w/w aqueous solutions of benzalkonium chloride which are available commercially as "BAC50".

Preferred cationic viral envelope/vesicle disruptor compounds include CHDG, N-(3-aminopropyl)-N-dodecylpropane-1,3-diamine, PHMB, DDAC and benzalkonium chloride, more preferably CHDG, N-(3-aminopropyl)-N-dodecylpropane-1,3-diamine, PHMB and benzalkonium chloride, even more preferably N-(3-aminopropyl)-N-dodecylpropane-1,3-diamine and PHMB, and most preferably N-(3-aminopropyl)-N-dodecylpropane-1,3-diamine.

Although mixtures of cationic viral envelope/vesicle disruptor compounds may be used, the sample is preferably mixed with no more than two such compounds. In one embodiment the sample is mixed with two cationic viral envelope/vesicle disruptor compounds. In another embodiment, the sample is mixed with one cationic viral envelope/vesicle disruptor compound.

The concentration of cationic disruptor compound in the mixture may be from 0.000005 to 0.01% v/v, preferably 0.00001 to 0.001, more preferably about 0.0001 to 0.0008% v/v. For example, if the cationic disruptor compound is used in the form of a 30% aqueous solution of N-(3-aminopropyl)-N-dodecylpropane-1,3-diamine (commercially available as Lonzabac® 12.30), a suitable concentration is about 1 part to 2000 parts, or about 1 part to 1000 parts, by volume of the mixture. In this paragraph, "mixture" refers to the mixture produced in Processing Methods B or C/C1/C2, i.e. the mixture provided by mixing the biological sample or the precipitate with:

i. at least one cationic viral envelope/vesicle disruptor compound, or at least one disulphide reducing agent, or a combination thereof; and ii. at least one mass spectrometry grade solvent.

If the cationic disruptor compound has a tendency to form micelles, it is preferably used at a concentration below its critical micelle concentration, as formation of micelles can interfere with the MALDI-ToF spectra. Critical micelle concentrations for some of the preferred cationic disruptor compounds are shown below. Values for other compounds will be available in standard reference texts or from suppliers.

| Cationic disruptor compound | Critical micelle concentration in mol/L |
| --- | --- |
| BAC | $4.4 \times 10^{-3}$ |
| DDAC | $3.5 \times 10^{-3}$ |
| CHDG | Does not form micelles |
| PHMB | $5 \times 10^{-2}$ |
| N-(3-aminopropyl)-N-dodecylpropane-1,3-diamine | about $2 \times 10^{-3}$ |

The cationic disrupter compounds are stable in solution at room temperature for over a year but the solutions should not be refrigerated or frozen as this may cause precipitation of the compounds, which may not be easily reversible.

The at least one disulphide reducing agent can release disulphide bound peptides or proteins of viral envelopes or viral capsids. These peptides or proteins may also act as markers of certain viral infections that are detectible in MALDI-ToF spectra. Without wishing to be limited by theory, it is believed that it may be possible to release exposed disulphide-bound peptides or proteins on the surface of a viral envelope or viral capsid without requiring a cationic disruptor compound. Thus, in an embodiment the sample is mixed with the at least one disulphide reducing agent, optionally in combination with the cationic viral envelope disruptor compound. When used together with a cationic disruptor compound, the disulphide reducing agent may also fragment the virus-originating envelope compounds, such as envelope proteins, extracted from the viral envelope and solubilized by the cationic disruptor compounds. These fragments may also be detected by MALDI-ToF MS and therefore act as markers of a viral infection.

Figure 6:
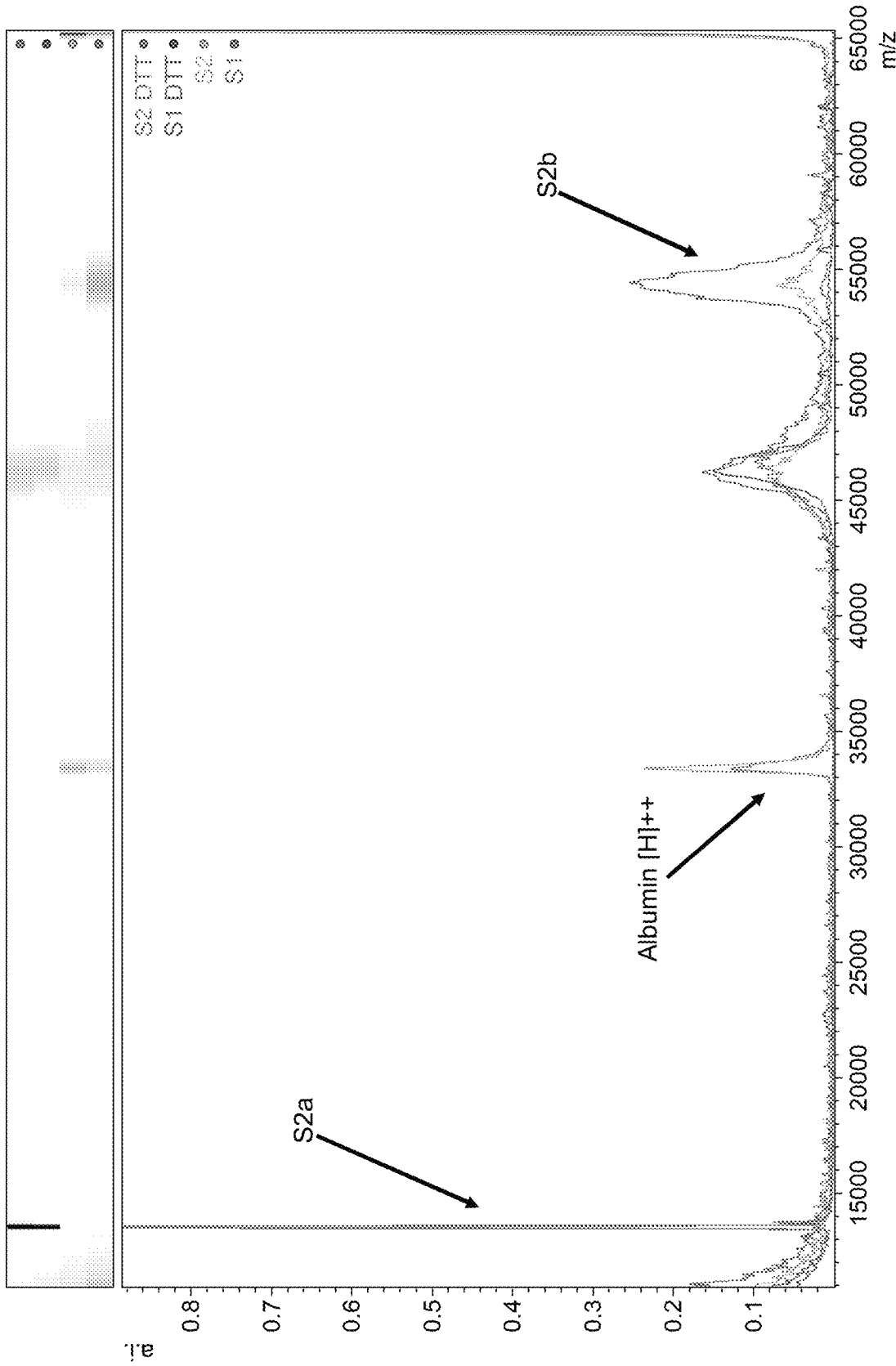

Comparing spectra obtained when using a cationic disruptor compound with and without a disulphide reducing agent can also provide important diagnostic information relating to cleaved large proteins such as surface spike and other entry receptors on the virion. For example, as shown in FIG. 6, treatment with a disulphide reducing agent, such as DTT, can liberate S2a and S2b fragments of spike proteins allowing such fragments to be detected by MALDI ToF MS.

Similarly, the at least one disulphide reducing agent can release disulphide bound peptides or proteins from extracellular vesicle or exosome membranes. These peptides or proteins may also act as markers for certain disease states that are detectible in MALDI-ToF spectra. Without wishing to be limited by theory, it is believed that it may be possible to release exposed disulphide-bound peptides or proteins on the surface of an exosome membrane without requiring a cationic disruptor compound. Thus, in an embodiment the sample is mixed with the at least one disulphide reducing agent, optionally in combination with the cationic disruptor compound. When used together with a cationic disruptor compound, the disulphide reducing agent may also fragment the membrane compounds, such as membrane proteins, extracted from the membrane and solubilized by the cationic disruptor compounds. These fragments may also be detected by MALDI-ToF MS and therefore act as markers of disease states.

A number of agents for reducing disulphide bonds in peptides and proteins are known in the art. Suitable such compounds include dithiothreitol (DTT), 2-mercaptoethanol (BME), 2-mercaptoethylamine hydrochloride (2-MEA-HCl), tris(2-carboxyethyl)phosphine (TCEP) and tris(2-carboxyethyl)phosphine hydrochloride (TCEP-HCl), 1,5-diaminonaphthalene (1,5-DAN) and combinations thereof, preferably DTT, TCEP or TCEP-HCl, particularly TCEP-HCl.

It is important that the disulphide reducing agents do not interfere with detection of the diagnostic virus-originating or vesicle-originating peaks or peak patterns in the MALDI-ToF spectra. Preferred examples of non-interfering disulphide reducing agent is DTT, TCEP or TCEP-HCl.

Although mixtures of disulphide reducing agents may be used the sample is preferably mixed with no more than two such compounds. In one embodiment the sample is mixed with two disulphide reducing agents. Preferably, the sample is mixed with one disulphide reducing agent.

If present, the concentration of disulphide reducing agent in the mixture may be less than 1 mol/L such as 0.8 mol/L or less, 0.6 mol/L or less, preferably 0.5 or less. Preferably the concentration of disulphide reducing agent is about 0.5 mol/L. In this paragraph, "mixture" refers to the mixture produced in Processing Methods B or C/C1/C2, or, for the process of claim 18, the mixture afforded when the disulphide reducing agent is added to the solution or suspension of the precipitate or when suspending the precipitate in a mass spectrometry grade solvent.

Mass spectrometry grade solvents are known in the art and are commercially available. They are highly purified to prevent interference with the spectra of the samples being analysed. Suitable such solvents for use in the present invention include methanol, acetonitrile (ACN), water (for example double distilled deionised water), trifluoroacetic acid (TFA), methylamine and combinations thereof, preferably methanol, acetonitrile (ACN), water (for example double distilled deionised water), and combinations thereof, more preferably water or a mixture of water and ACN, most preferably water. Undesirable micelle formation, which may interfere with the MALDI-ToF MS, can be limited by excluding TFA and/or by using mixtures of water and ACN, for example in a v/v ratio of from 6:4 to 0.5:9.5 (acetonitrile water), preferably about 10% v/v ACN in water. Preferably, the water is double distilled deionised water.

Without wishing to be bound by theory, the inventors believe that protonation or deprotonation of viral marker or vesicle proteins may cause marker coagulation or adherence, thereby preventing their detection by MALDI-ToF MS. Preferably, the pH of the mixture of the biological sample, the mass spectrometry grade solvent and the cationic disruptor compound(s) and/or the reducing agent(s) is from 5 to 10, more preferably from 6 to 8, more preferably from 6.5 to 7.5. Most preferably, the solvent pH is about 7, such as from 6.9 to 7.1.

An especially preferred mass spectrometry grade solvent is double distilled deionised water having a pH of 6.998. This is commercially available, for example from ROMIL, Cambridgeshire, UK.

Without wishing to be bound by theory, the inventors believe that the identity of the cationic disruptor compound influences the molecular weights of the virus-originating envelope compounds that are preferentially solubilized from the viral envelope, or the molecular weights of the biomarkers such as proteins from exosomes or other extracellular vesicles. For example, the inventors have found that treatment with CHDG is particularly suitable for detection of low-molecular weight (e.g. from 1000 to 30000 m/z) and high-molecular weight (more than 60000 m/z) markers, such as virus-originating markers. Benzalkonium chloride is particularly suitable for detection of medium-molecular weight (more than 30,000 to 60,000 m/z) markers, such as virus-originating markers. N-(3-aminopropyl)-N-dodecylpropane-1,3-diamine is particularly suitable for detection of low- and medium-molecular weight markers. PHMB is particularly suitable for detection high-molecular weight markers.

Figure 2:
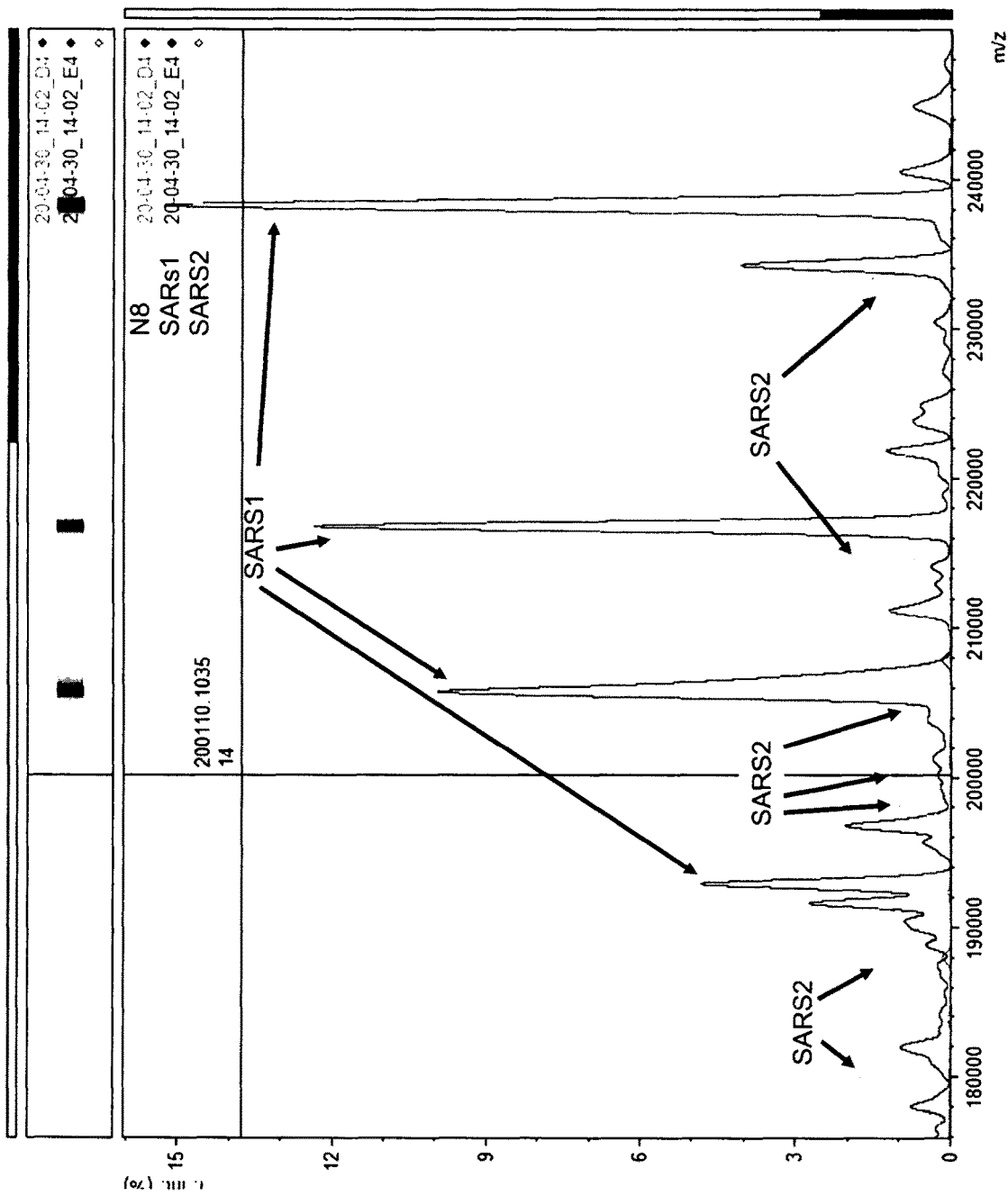
FIG. 2 is a MALDI-ToF mass spectrum showing a number of peaks which are indicative of SARS1 and SARS2 pseudoviruses for a higher m/z range than FIG. 1.
Figure 3:
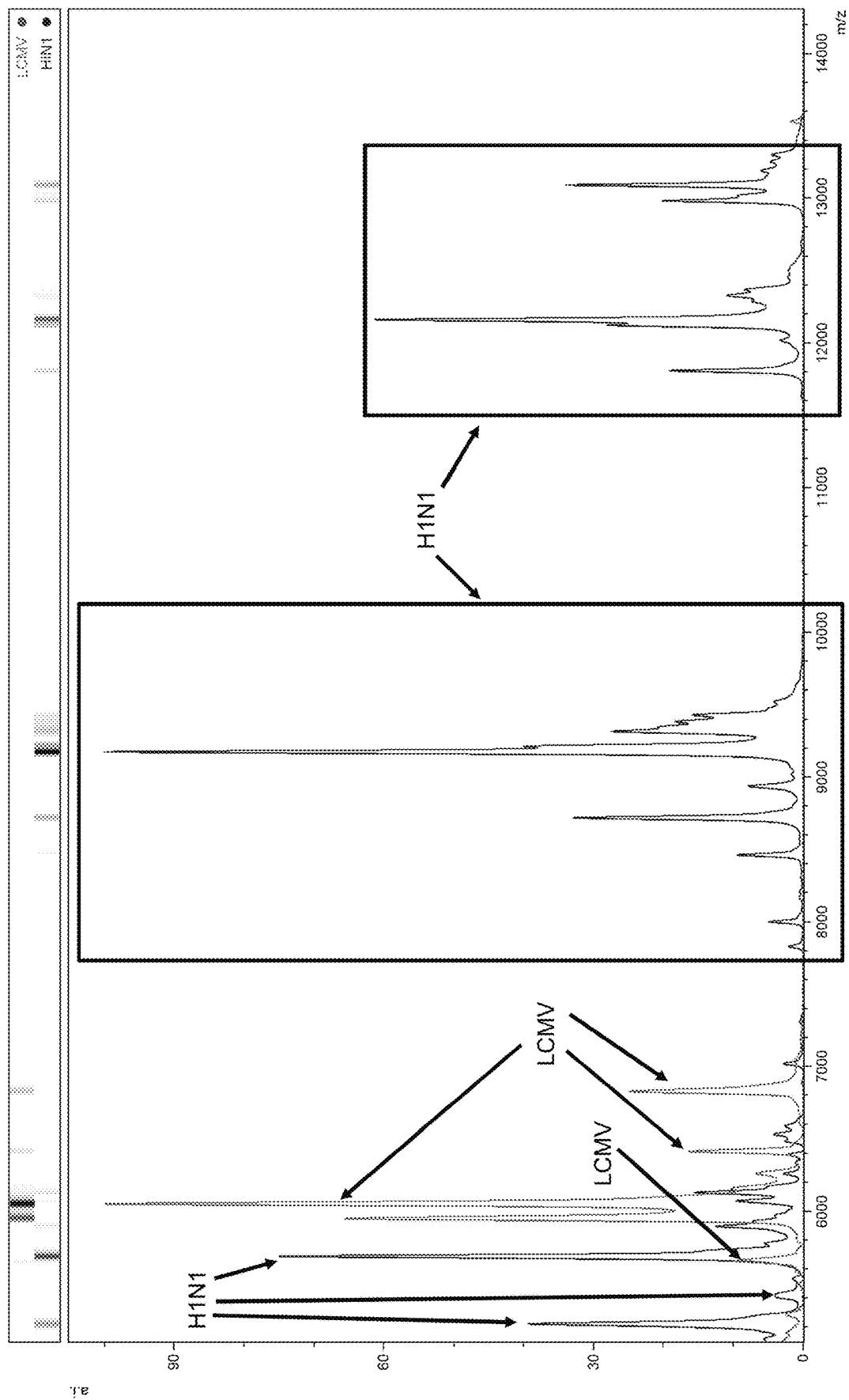
Figure 4:
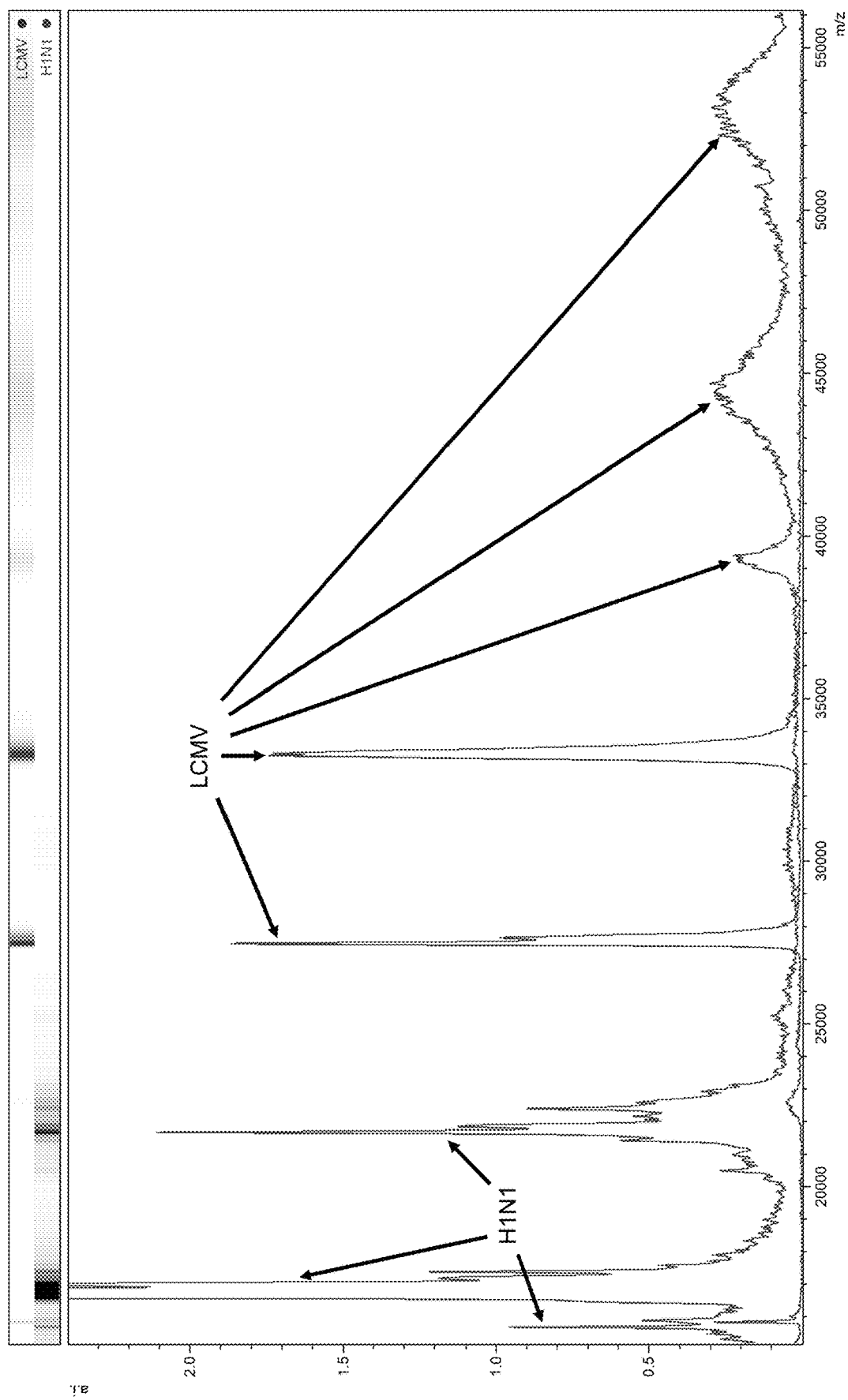
Figure 5:
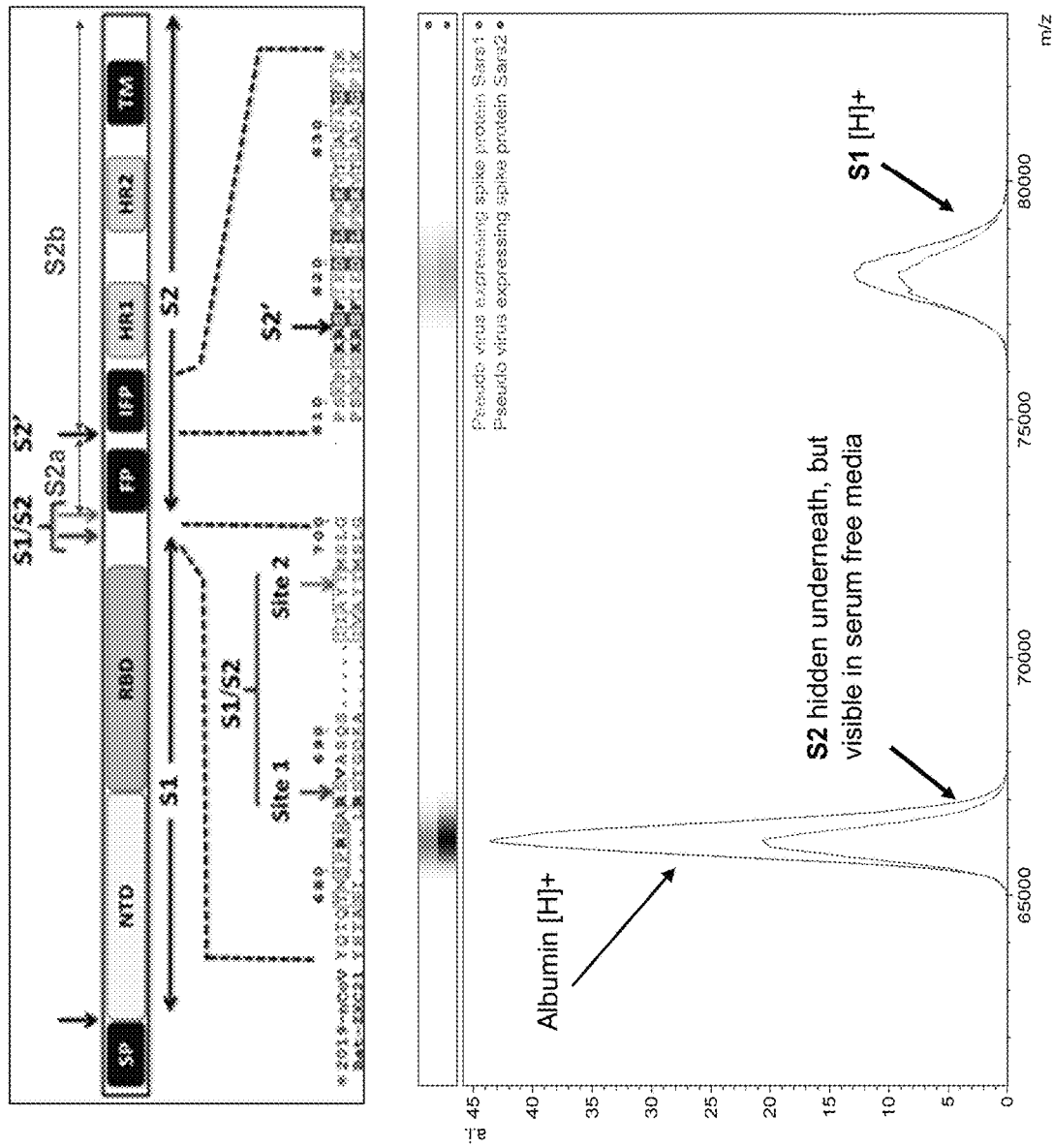

The optimum choice of disruptor compounds may therefore vary depending on the candidate virus and the diagnostic marker peaks/peak patterns selected for enabling diagnosis of a viral infection. For example as, shown in FIG. 2, the inventors have identified peaks indicative of SARS-CoV-1 and SARS-CoV-2 at m/z values of from about 180000 to about 245000 and so treatment of a disruption buffer comprising PHMB may enable diagnosis of SARS-CoV-1 or SARS-CoV-2 through detection of high molecular weight markers in this region of a MALDI-ToF spectrum.

Preferred cationic disruptor compounds for the detection of low molecular weight protein or protein fragment (e.g. peptide) markers (1000 to 30,000 m/z) include CHDG, N-(3-Aminopropyl)-N-dodecylpropane-1,3-diamine or a combination thereof.

Preferred cationic disruptor compounds for the detection of medium molecular weight protein markers (more than 30,000 to 60,000 m/z) include N-(3-Aminopropyl)-N-dodecylpropane-1,3-diamine and benzalkonium chloride or a combination thereof.

Preferred cationic disruptor compounds for the detection of high molecular weight protein markers (more than 60,000 to 100,000 m/z) include CHDG, PHMB or a combination thereof. For detection of even higher molecular weight proteins, PHMB is preferred, such as PHMB without a disulphide reducing agent.

As shown in FIGS. 1, 3, 4, 7, 9 and 12 and 13, the inventors have found that treatment with N-(3-aminopropyl)-N-dodecylpropane-1,3-diamine (Lonzabac) and DTT allows markers having m/z values of about 1,000 up to about 60000 to be efficiently detected. The inventors have identified a number of diagnostic virus-originating peaks/peak patterns in this m/z range for a variety of viruses, including SARS-CoV-1, SARS-CoV-2, MERS-CoV, H1N1 influenza strains (e.g. A/Puerto Rico/8/1934 (H1N1) and A/England/195/2009) and LCMV. In a particularly preferred embodiment, the sample is mixed with N-(3-aminopropyl)-N-dodecylpropane-1,3-diamine and DTT. In this embodiment, the mass spectrometry grade solvent is preferably double distilled deionised water.

In another preferred embodiment, the sample is mixed with N-(3-aminopropyl)-N-dodecylpropane-1,3-diamine and TCEP.

In another particularly preferred embodiment, the sample is mixed with N-(3-aminopropyl)-N-dodecylpropane-1,3-diamine and TCEP-HCl.

Enrichment of Virion Particles, Exosomes or other Extracellular Vesicles by Precipitation and Separation from Supernatant It is desirable to concentrate any candidate virion particles by precipitation prior to MALDI-ToF MS analysis to reduce signal(s) from proteins (such as albumin in the case of blood-derived biological samples) or other compounds that may be present in the sample and which do not originate from the candidate virus. Thus, in one aspect the invention is directed to preparation method A and methods for analysing a biological sample for the presence of a virus using MALDI-ToF MS, wherein the biological sample has first been processed according to preparation method A.

It is also desirable to concentrate any candidate exosomes or other extracellular vesicles by precipitation prior to MALDI-ToF MS analysis to reduce signal(s) from proteins (such as albumin in the case of blood-derived biological samples) or other compounds that may be present in the sample and which do not originate from the exosome or other extracellular vesicles. Thus, in one aspect the invention is directed to preparation method A and methods for analysing a biological sample for the presence of an exosome or other extracellular vesicle using MALDI-ToF MS, wherein the biological sample has first been processed according to preparation method A.

Known enrichment and purification techniques are time consuming, expensive and often require large sample volume. An advantage of preparation method A is that further purification steps may not be required.

Depending on the conditions, precipitation can introduce factors detrimental to MALDI-ToF MS analysis such as high ion content, chemical residue impurities and/or polymers. For example, the inventors have found that the type of precipitation-inducing agent, temperature and pH can affect whether virus markers can be detected by MALDI-ToF MS. In order for a viral marker, such as a virus-originating protein or fragments thereof, to be detectable by MALDI-ToF MS the precipitation procedure should not induce coagulation or adherence of the markers, either to one another or to other components of the sample such as lipid/cholesterol clumps.

Similarly, in order for a marker, such as an exosome- or other extracellular vesicle-originating protein or fragments thereof, to be detectible by MALDI-ToF MS the precipitation procedure should not induce coagulation or adherence of the markers, either to one another or to other components of the sample such as lipid/cholesterol clumps.

The inventors have found that salt-induced precipitation introduces too many contaminating ions into the precipitate, which interferes with the MALDI-ToF spectroscopy. It was also found that PEG-induced precipitation introduces PEG polymer peaks that dominate the MALDI-ToF spectra so that virus-derived peaks of interest could not be observed. Surprisingly, precipitation induced by mixing with a volatile organic solvent at a temperature of −25° C. to 18° C. did not introduce contaminants that prevented detection of diagnostic virus protein marker peaks by MALDI-ToF MS.

As used herein, the term volatile refers to solvents having a boiling point of less than 98° C., preferably less than 85° C. at 760 mmHg (101 kPa). For example, the volatile organic solvent may be selected from acetone, a $C_{1-3}$ alcohol, ethyl acetate, butanone, chloroform or mixtures thereof. Preferably, the volatile solvent is miscible with water. Preferably, the volatile organic solvent is selected from acetone, or a $C_{1-3}$ alcohol, more preferably from acetone, ethanol or isopropanol, and even more preferably from acetone or isopropanol. Most preferably, the volatile organic solvent is acetone.

Particularly preferred organic solvents are those that inactivate virion particles. For example, acetone has been show inactivate enveloped viruses, such as respiratory syncytial virus and SARS-CoV-1 (see D. Bardell, Journal of Clinical Microbiology, February 1975, p. 157-160 and Kariwa et al. Japanese Journal of Veterinary Research (2004) 52(3): 105-112 respectively). Use of acetone as the volatile solvent is therefore preferred for safety reasons and for reducing the sterilisation burden for the MALDI-ToF MS hardware used to run the mass spectra on the treated samples Whilst the inventors found that use of ethanol led to residues in MALDI-ToF spectra, ethanol may still be suitable provided that the residue peaks do not obscure the diagnostic virus-originating, exosome-originating or other extracellular vesicle-originating peaks or peak patterns in the MALDI-ToF spectra. Such residue peaks were not observed when acetone was used. Thus, in some embodiments, the volatile organic solvent is not ethanol. Chloroform can be hazardous and may dissolve certain polymers. Thus, in some embodiments, the volatile organic solvent is not chloroform.

Preferably, the volatile organic solvent is sufficiently pure to avoid impurity peaks appearing in the MALDI-ToF spectra.

The temperature of the volatile solvent in the precipitation process is from −25° C. to 18° C., preferably from −10 to 18° C. Without wishing to be bound by theory, the inventors believe that as the temperature is increased, higher molecular weight proteins and virion particles are preferentially brought into the precipitate and thereby separated from small to mid-sized proteins derived from culture media, any serum, and/or from the non-viral elements (or the non-exosome/non-vesicle elements) of the biological sample which may also be brought into the precipitate at lower temperatures. Accordingly, higher temperatures above 0° C., such as from 0 to 18° C., are preferred since this ensures that a greater proportion of the peaks in the MALDI-ToF spectra are virus-derived, thereby facilitating identification of diagnostic peaks and peak patterns originating from the candidate viruses, such as peaks from viral spike proteins or fragments thereof. More preferably, the temperature is from 2 to 10° C., even more preferably from 3 to 8° C., most preferably from 4 to 6° C. These preferred temperatures of the volatile solvent also apply to the precipitation of exosomes or other extracellular vesicles.

Operating at temperatures above 0° C. is also easier for practical reasons. For example, the volatile solvents can then be cooled in ice or using a conventional refrigerator.

The inventors have also surprisingly found that the pH during the treatment to form the precipitate, and during any subsequent resuspension or dissolution of the precipitate in a mass spectrometry grade solvent, may influence whether virus markers can be detected by MALDI-ToF MS. The inventors surprisingly found that no virus markers were observable when the precipitation was carried out at pH 3 and that the virus marker peaks were reduced significantly when it was carried out at pH 8. Without wishing to be bound by theory, the inventors believe that protonation or deprotonation of viral marker proteins may cause protein coagulation or adherence, thereby preventing their detection by MALDI-ToF MS. Preferably, the pH during the precipitation treatment is from 5 to 10, more preferably from 6 to 8, more preferably from 6.5 to 7.5. Most preferably, the pH is about 7, such as from 6.9 to 7.1. These preferred pH ranges/values also apply to the precipitation of exosomes or other extracellular vesicles.

Any known technique for separating the precipitate from the supernatant may be used. Preferably, the precipitate is separated from the supernatant by centrifugation. The centrifugal acceleration may be from 5,000-35,000 g, such as from 10,000-25,000 g, more preferably from 12,000 to 18,000 g, most preferably from 15,000 to 17,000 g. The centrifugation may be conducted for a duration of from 5 minutes to 1 hour, such as from 10 minutes to 40 minutes, most preferably from 20 to 35 minutes. Preferably, the centrifuge is maintained at a temperature of from −25° C. to 18° C. The preferred ranges for the volatile solvent precipitation temperature disclosed herein also apply to the centrifuge.

When retaining the precipitate, for ease of handling a small amount, such as up to about 20 µL, of supernatant can be retained with the precipitate before analysing the precipitate by MALDI-ToF MS or further processing the precipitate prior to MALDI-ToF MS, for example according to processing method B.

If the biological sample has been cultured as described above, the ratio (v/v) of cell culture media to volatile organic solvent may range from 2:1 to 1:5 (volatile organic solvent: cell culture). Preferably, the ratio is from 1.5:1 to 1:4. More preferably, the ratio is from 1:1 to 1:3.

MALDI-ToF Mass Spectrometric Analysis and Identification of any Virus, or Exosome or other Extracellular Vesicle, Marker Peaks After processing a sample according to preparation method A, the precipitate may be suitable for direct MALDI-ToF MS analysis (provided the precipitate is suspended or dissolved in a mass spectrometry grade solvent, such as those described above) or the precipitate may be further processed, for example according to processing method B, prior to MALDI-ToF MS analysis.

Accordingly, another aspect of the invention is a method for analysing a biological sample for the presence of a virus, or an exosome or other extracellular vesicle, the method comprising: treating the sample at a temperature of from −25° C. to 18° C. with a volatile organic solvent to form a precipitate comprising any virions, exosomes or other extracellular vesicles present in the sample; separating the precipitate from the supernatant; dissolving or suspending the precipitate in a mass spectrometry grade solvent; and subjecting the solution or dispersion to MALDI-ToF mass spectrometric analysis. Optionally, before subjecting the solution or dispersion to MALDI-ToF mass spectrometric analysis, the precipitate may be treated with a disulphide reducing agent, such as those described above.

Following the dissolution or suspension of the precipitate for MS analysis, the pH is preferably from 5 to 10, more preferably from 6 to 8, more preferably from 6.5 to 7.5. Most preferably, the pH is about 7, such as from 6.9 to 7.1

The MALDI-ToF mass spectrometric analysis may comprise applying the processed sample and a solution comprising a MALDI-ToF matrix material to a MALDI-ToF target plate. Any known procedure for applying the analyte sample and matrix material solution to the target plate may be used. Suitable MALDI-ToF matrix material and solvents for the MALDI-ToF matrix material solution are well known in the art and are commercially available. For example, suitable matrix materials include sinapinic acid, α-cyano-4-hydroxycinnamic acid (HCCA), 2,5-dihydroxybenzoic acid (2,5-DHB), 2-acetyl-1,4-dihydroxybenzene (also known as 2,5-dihydroxyactetophenone [2,5-DHAP]), a 9:1 w/w mixture of 2,5-DHB and 2-hydroxy-5-methoxybenzoic acid (SDHB), 3-hydroxypicolinic acid (3-HPA), 1,5-diaminonaphthalene (1,5-DAN), ferulic acid or picolinic acid. Preferably, the matrix material is sinapinic acid. Preferably, the solvent for the matrix material is a mixture of acetonitrile, water and trifluoroacetic acid, such as a 1:1 mixture (by volume) of 0.1% v/v aqueous TFA and acetonitrile.

Figure 7:
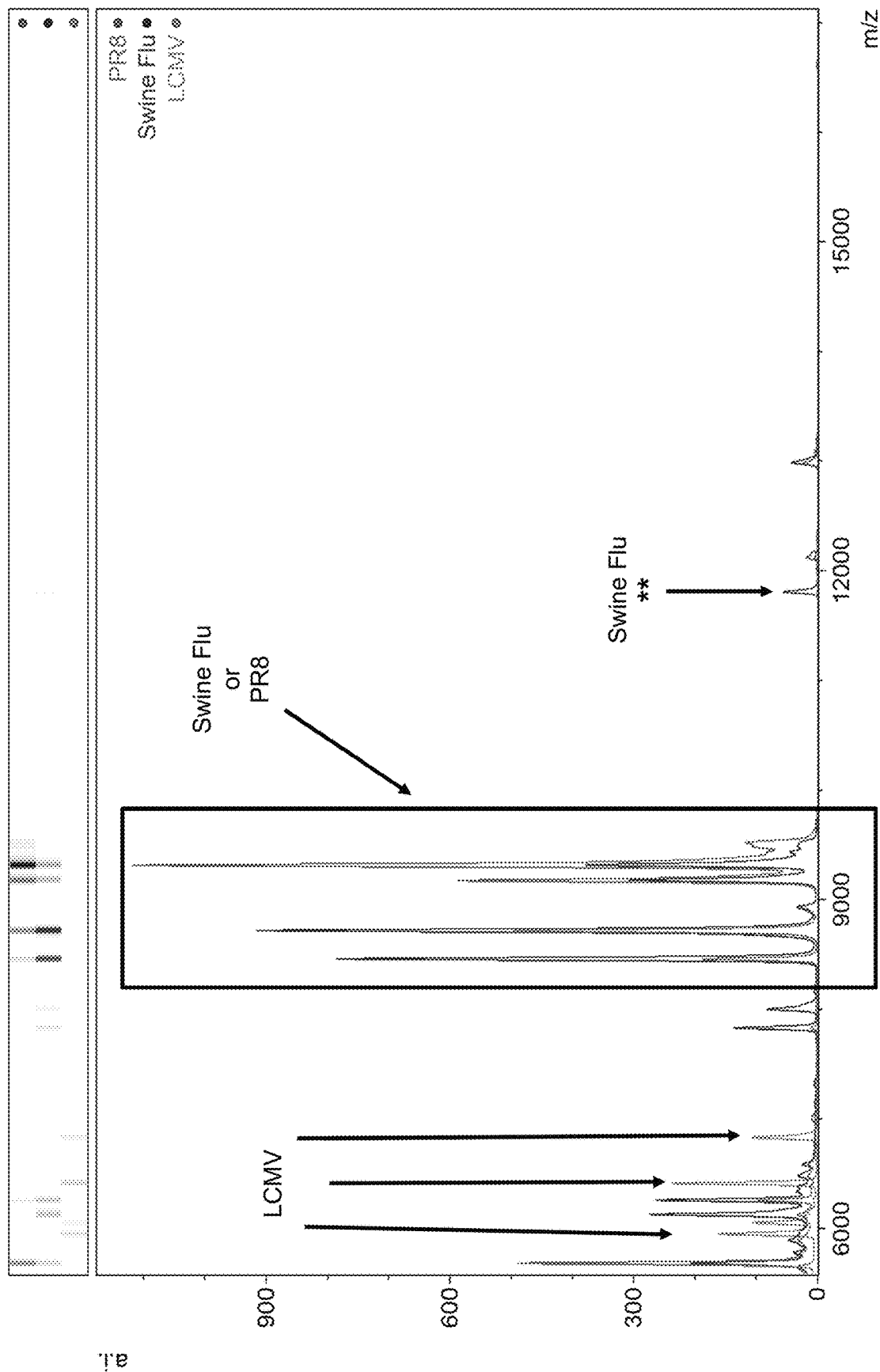
Figure 8:
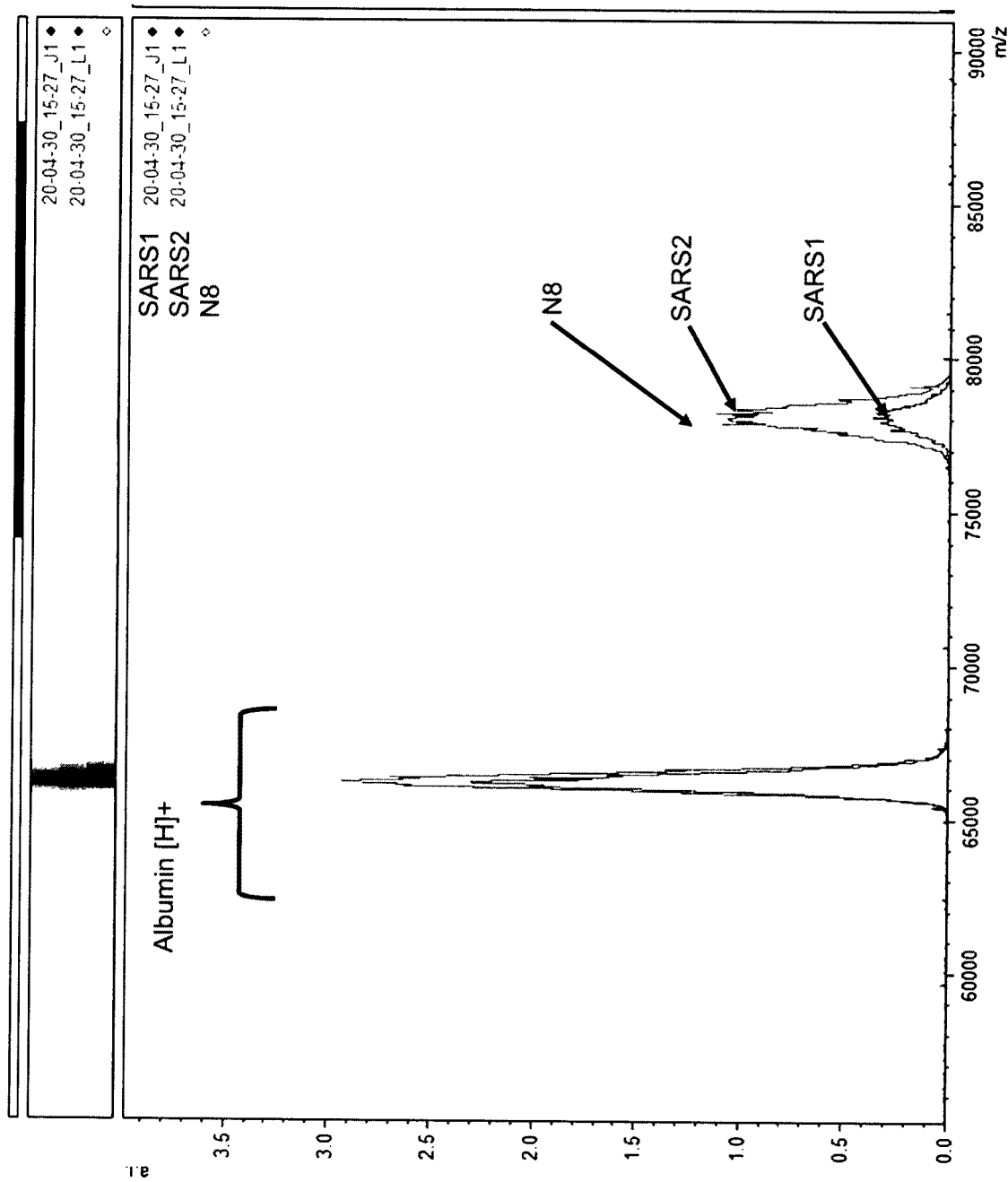
Figure 9:
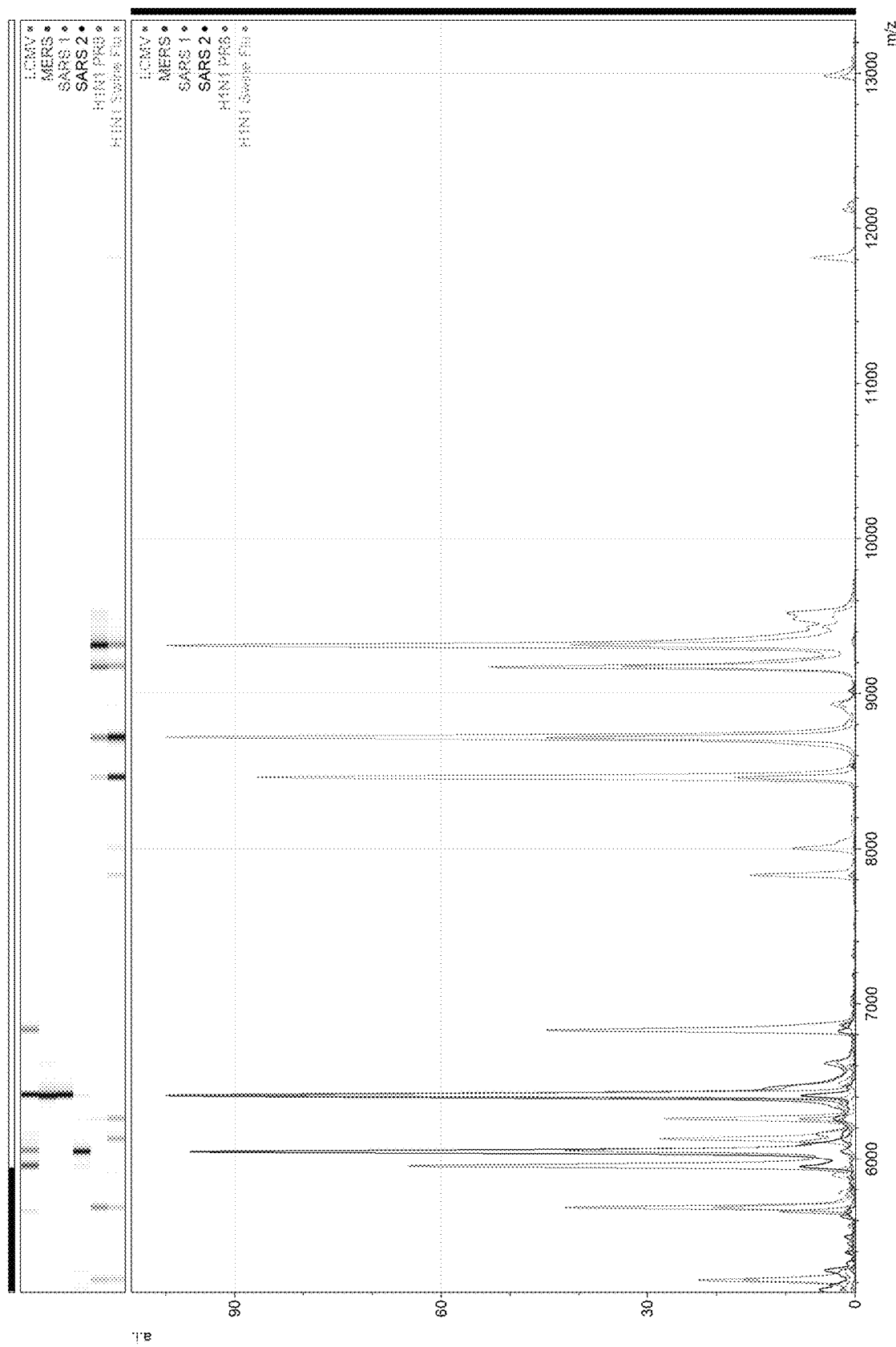

The presence of any candidate virus in the biological sample can be detected by identifying the diagnostic peaks or peak patterns in the MALDI-ToF spectra which are indicative of the candidate virus. The diagnostic peaks or peak patterns for a given virus can be identified from reference spectra obtained from samples known to contain the virus(es) of interest. For example, the inventors have identified a number of peaks in the m/z ranges about 12000 to about 14000 and about 180,000 to about 245,000 that are indicative of SARS-CoV-2 and SARS-CoV-1 and are believed to correspond to spike protein fragments (see FIGS. 1 and 2). The inventors have also identified peaks at m/z values of 9200 and 44000 that are indicative of influenza N9 and N8 respectively (see FIGS. 10 and 11). FIG. 7 shows that two strains of H1N1 (A/Puerto Rico/8/1934 and A/England/195/2009) can be distinguished by the presence of a peak at about 11800 m/z in A/England/195/2009 but not A/Puerto Rico/8/1934.

Suitable diagnostic peaks or peak patterns for novel viruses can be identified by processing and analysing a sample known to contain the candidate virus using a method of the invention. The MALDI-ToF detector can then be tuned to detect ions in the m/z region containing the diagnostic peaks or peak patterns of interest.

The presence of any candidate biomarker from an exosome or other extracellular vesicle in the biological sample can be detected by identifying the diagnostic peaks or peak patterns in the MALDI-ToF spectra which are indicative of the candidate biomarker. The diagnostic peaks or peak patterns for a given biomarker can be identified from reference spectra obtained from samples known to contain the biomarker(s) of interest.

Suitable diagnostic peaks or peak patterns for novel exosomes or biomarkers can be identified by processing and analysing a sample known to contain the candidate exosome or biomarker using a method of the invention. The MALDI-ToF detector can then be tuned to detect ions in the m/z region containing the diagnostic peaks or peak patterns of interest.

If the preparation procedure involves first culturing the biological sample, peaks in the MALDI-ToF spectra derived from the culture medium (for example from any serum present) can be identified by comparing the spectra obtained with that of a control sample obtained by processing the culture media absent any biological sample.

The inventors have observed a peak at 8,550 m/z in the MALDI-ToF spectra for all the tested viruses corresponding to ubiquitin. Excessive ubiquitin production is believed to be a mammalian cell anti-virus response to initial viral infection by many viruses. The presence of the ubiquitin peak is therefore not diagnostic of the presence of a particular virus, but may be used as an indicator of a viral infection.

The virus-originating, exosome-originating or other extracellular vesicle-originating markers that may be detected using the methods of the invention span a wide range of molecular weights. Optimization of sensitivity for large markers, such as proteins, may be achieved by high ion gating (10,000 m/z plus) and higher detector voltages.

In order to see clear peaks in MALDI-ToF spectra, particularly for high molecular weight markers, it may be necessary to use known data processing techniques to account for broadening of peaks. For example, isotopic variation in a viral markers, such as a virus-originating peptide or protein, may lead to mass variation of the marker and therefore to broadening of the corresponding peak in a MALDI-ToF spectra. For small peptides (m/z of from about 200 to 1000), large peptides/small proteins (m/s of from above 1000 to 30000), medium mass proteins (m/z of above 30000 to 60000) and large proteins/glycoproteins (m/z of above 60000) Gaussian averaging of 1-5 m/z, 10-30 m/z, 50-100 m/z or 500-1000 m/z respectively may need to be applied.

The spectrum recording and analysis will ideally be automated to allow rapid throughput of multiple samples. The analysis methods of the invention therefore lend themselves to screening of multiple biological samples for the presence or absence of viruses, exosomes or other extracellular vesicles.

The analysis methods can be used to diagnose viral infection in a patient by testing a sample from the patient for the presence of the virus in question. Alternatively, the results of the analysis may show that no virus is present, thus allowing screening of individuals after potential exposure to a virus. The methods of the invention may be of particular benefit in detecting individuals who are carrying a virus, and hence are potentially infectious, but who are pre-symptomatic or asymptomatic.

It may also be desirable to combine the results of the methods of the invention with those of a second analysis method, in order to confirm infection with a particular viral strain.

When analysing saliva samples, in order to determine if a negative is a true negative, the presence of non-digestive (ND) mucus gel non-mucin structural proteins found in oral and respiratory mucus and saliva can be monitored for in the samples. Peaks at 10,900 to 11,900 m/z correspond to ND non-mucin proteins co-precipitating with MUC-glycoproteins during acetone extraction of samples. ND non-mucin proteins are only liberated from the viscous mucous gel complex by extensive disulphide reduction. The 10,900 to 11,900 m/z proteins are endogenous compounds of oral respiratory tract mucus and saliva (Meldrum, O. W., Yakubov, G. E., Bonilla, M. R. et al. Mucin gel assembly is controlled by a collective action of non-mucin proteins, disulfide bridges, $Ca^{2+}$-mediated links, and hydrogen bonding. Sci Rep 8, 5802 (2018). https://doi.org/10.1038/s41598-

018-24223-3). These peaks should always be present in a correctly collected gargle-saliva sample mass spectra. If a peak at 10,900 to 11,900 m/z peak is not present, this indicates that the sample is in a poor condition and the result should be disregarded.

In addition to identifying peaks in the spectra of saliva samples which are derived from a virus such as the SARS-CoV-2 virus, it can be beneficial to identify whether or not other maker(s) of elevated immunological activity within the oral mucosa of the upper respiratory tract are present in the mass spectra, for example by measurement of peaks relating to the IgA heavy chain to see if they exceed a predetermined threshold value.

The analysis methods of the invention also lend themselves to screening of multiple biological samples for the presence or absence of biomarkers derived from exosomes or other extracellular vesicles. The analysis methods can be used to diagnose infection in a patient by testing a sample from the patient for the presence of the biomarker in question. Alternatively, the results of the analysis may show that no biomarker is present, thus allowing screening of individuals for the presence or absence of a disease.

EXAMPLES

Materials

N-(3-Aminopropyl)-N-dodecylpropane-1,3-diamine: Lonzabac™ 12.30 from Lonza (referred to below as "Lonzabac").
Benzalkonium chloride: BAC50 (50% v/v aqueous solution).
Chlorhexidine gluconate (CHDG): 19-21% w/v aqueous solution from Medichem, S.A.
Polyhexamethylene biguanide hydrochloride (PHMB): Acticide PHB 20 from Thor Specialites (UK) Limited.
Acetone: Analar grade
DTT: 1 M solution in ddH$_2$O or 1 M solution in 10% ACN/90% (v/v) ddH$_2$O Tris(2-carboxyethyl)phosphine hydrochloride, (TCEP-HCl) from Sigma (CAS number 51805-45-9)

Example 1

Preparation of Cell Cultures Comprising Virus Infected Human Cells 0.1 µL to 100 µL of biological samples spiked with virus particles selected from: lentiviral pseudotypes forming plasmids bearing the SARS-CoV-1 (SARS1) spike protein, SARS-CoV-2 (SARS2) spike protein, MERS-CoV spike protein, influenza N8 neuraminidase, or influenza N9 neuraminidase; Lassa virus (LASV); lymphocytic choriomeningitis virus (LCMV); Influenza A/Puerto Rico/8/1934 (PR8) or Influenza A/England/195/2009 (Swine Flu) were added to 200 μL-5 mL of cell culture media (such as minimum essential medium [MEM]) containing penicillin and streptomycin. The sample inoculated culture medium was added to washed viral receptive cell line (for example Vero C1008 [Vero 76, clone E6, Vero E6] (ECACC 85020206) or human embryo kidney cell lines such as 293 [ECACC 85120602]) and grown in 96-well plates for 24 hours. For some samples (FIGS. 5, 6, 8 and 10) fetal bovine serum was present in the cell growth media.

Example 2

Precipitation of Virion Particles from Biological Samples

Virus-containing culture medium obtained by the procedure of Example 1 was mixed with ice-cold (4° C.) acetone in a volume (v/v) ratio of 1:1, 1:2 or 1:3 (acetone:sample). The mixture was then centrifuged in a refrigerated centrifuge (4° C.) at 16000 g for 30 minutes. The majority of the supernatant was removed to leave precipitate in the form of a pellet in up to approximately 20 μL of supernatant.

MALDI-ToF MS analysis after mixing the precipitate with one or more viral envelope disruptor compounds and/or DTT, and one or more mass spectrometry grade solvents (as set out in Example 3 below) showed that the acetone treatment did not introduce residues visible in the spectra.

Ethanol was also tested in place of the acetone. It was found that ethanol evaporation leaves residues visible in the MALDI-ToF spectra.

Comparative precipitation methods were also performed. It was found that salt-induced precipitation introduces too many contaminating ions into the precipitate, which interferes with the MALDI-ToF spectroscopy. It was also found that PEG-induced precipitation introduces polymer peaks that dominate the MALDI-ToF spectra so that virus-derived peaks of interest could not be observed.

Example 3

Viral Envelope Protein Release and MALDI-ToF MS Analysis

Pellets obtained according to the procedure of Example 2 were resuspended in 50 μL of double distilled deionised water (pH 6.998) [dd$H_2O$]. 2 μL of the solubilized pellet was mixed with 2 μL of disruption buffer.

The following disruption buffers were tested:

0.001% (v/v) Lonzabac and 1 M DTT in dd$H_2O$ (FIGS. 3, 4, 6, 7, 9 and 12-14))

0.001% (v/v) Lonzabac and 1 M DTT in 10% ACN/90% (v/v) dd$H_2O$ (FIG. 1)

0.001% (v/v) Lonzabac in dd$H_2O$ (FIGS. 5, 6 and 12-14)

PHMB in 10% ACN/90% (v/v) dd$H_2O$ (FIG. 2)

PHMB and 1 M DTT in dd$H_2O$ (FIGS. 12-14)

PHMB in dd$H_2O$ (FIGS. 12-14)

1 M DTT in dd$H_2O$ (FIG. 8)

1 part 0.0001% chlorohexidine gluconate (CHDG) in mass spectrometry grade pure $H_2O$ (pH 6.998), 1 part 0.00001% BAC50 in 50% acetonitrile (ACN)/50% mass spectrometry grade pure $H_2O$ (pH 6.998) (FIG. 11)

The mixtures were then analysed directly by MALDI-ToF MS.

A sandwich method of plating was used. An initial layer (1 μl) of matrix solution was spotted on the wells of stainless steel MALDI ToF target plates and left to air dry or dried on a hot plate at 30° C. The matrix solution was a solution of 20 mg/mL sinapinic acid in 0.1% v/v aqueous TFA/acetonitrile (50/50 v/v) (pH 2.8). 1 μL of the mixture of solubilised precipitate and disruption buffer was then spotted onto a well with the dry matrix and a further 1 μL of matrix solution was added to the wet sample spot and then left to dry to allow crystallisation.

MALDI-ToF spectra were recorded using a bench top Shimadzu Kratos 8020 MALDI-ToF mass spectrometer designed and manufactured to IS09001:2015 and ISO 13485:2016 quality management standards.

Spectra were analysed and processed (including any necessary peak smoothing) using the mMAS software. Various spectra are shown in FIGS. 1-14.

FIG. 1 is a MALDI-ToF mass spectrum showing peaks which are indicative of SARS-CoV-1 (SARS1) and SARS-CoV-2 (SARS2) pseudoviruses. The samples were subjected to acetone precipitation as described in Example 2. After precipitation, the samples were mixed with Lonzabac, DTT, acetonitrile and mass spectrometry grade pure water. FIG. 1 shows that SARS1 can be distinguished from SARS2 by the presence of the peaks at about 12,000 to 12,500 m/z for SARS1. The sample containing N8 pseudovirus was used as a control. As can be seen from FIG. 1, no peaks from the control obscured the SARS1 and SARS2 peaks.

FIG. 2 is a MALDI-ToF mass spectrum showing a number of peaks which are indicative of SARS1 and SARS2 pseudoviruses for a higher m/z range than FIG. 1. The samples were subjected to acetone precipitation as described in Example 2. After precipitation, the samples were mixed with PHMB and the solvents acetonitrile and mass spectrometry grade pure water. The samples were not treated with a disulphide reducing agent. FIG. 2 shows a number of peaks at high m/z values indicative of SARS1 and SARS2 that are not present in the N8 pseudovirus control, which are believed to correspond to spike protein fragments. These high m/z peaks were only observed when PHMB was used as the cationic viral envelope disruptor compound. As with FIG. 1, the sample containing N8 pseudovirus was used as a control.

FIGS. 3 and 4 are MALDI-ToF mass spectra for samples containing live H1N1 influenza virus (Influenza A/England/195/2009) and lymphocytic choriomeningitis virus (LCMV). The samples were subjected to acetone precipitation as described in Example 2 (which inactivated the viruses). After precipitation, the samples were mixed with Lonzabac and DTT. The spectra in FIGS. 3 and 4 shows clear differences in peak patterns between Influenza A/England/195/2009 and LCMV over different m/z ranges.

FIG. 5 shows a MALDI-ToF mass spectrum for samples containing SARS1 and SARS2 pseudoviruses together with a schematic of the spike protein structure. The samples were subjected to acetone precipitation as described in Example 2. After precipitation the samples were treated with Lonzabac. The samples were not treated with any disulphide reducing agent.

The spike proteins of SARS-COVID viruses are cleaved and matured into at least two fragments S1 and S2. The position of amino acid cleavage sites and the resultant fragment proteins are shown in the upper diagram in FIG. 5. The predicted mass of the disulphide bridge reduced proteins/protein fragments along with potential mass modification by N-linked glycosylation are shown in the table below (Table 1). As can be seen in the MALDI-ToF spectrum of FIG. 5, S2 fragments of SARS-CoV-1 and SARS-COV-2 spike proteins may be obscured by albumin originating from serum in the cell culture medium. These proteins are however observed in spectra run on samples cultured in serum-free culture media.

TABLE 1

| Fragment | peptide mass | N-Glycan mass | Expected m/z of N-glycopeptide | If cleaved at Furin S2 (−1,038 m/z) |
|---|---|---|---|---|
| S | 139,731 | 14,400-30,800 | 154,000-170,531 | N/A |
| S1 | 75,243 | 9,000-19,800 | 84,243-95,043 | Peptide-76,281 Glyco-peptide 84.5k-95.1k m/z |
| S2 | 64,505 | 5,400-11,000 | 69,905-75,505 | Peptide-63,467 Glyco-peptide 68.8k-75.5k m/z |
| S2a | 14,133 | 1,800-4,400 | 15,933-18,533 | Peptide 13,095 Glyco-peptide 13.9k-18.5k m/z |
| S2b | 50,390 | 3,600-6,600 | 53,990-56,990 | 53,990-56,990 | k = thousand

FIG. 6 shows a MALDI-ToF mass spectrum for samples containing SARS1 and SARS2 pseudoviruses. The samples were subjected to acetone precipitation as described in Example 2. After precipitation the samples were treated with Lonzabac. in double distilled deionised water ($ddH_2O$) with and without a disulphide reducing agent (DTT). FIG. 6 shows that mixing with DTT, in addition to Lonzabac and $ddH_2O$, reduced the S1 peak and the S2 peaks (seen in serum free cultures). Numerous lower mass peaks are only seen in samples solubilized with DTT added. These included peaks with masses closely matching that of fragment S2a.

FIG. 7 shows a MALDI-ToF mass spectrum for samples containing live Influenza A/Puerto Rico/8/1934 (PR8) virus, Influenza A/England/195/2009 (Swine Flu) virus and lymphocytic choriomeningitis virus (LCMV). Virus was grown on mammalian cells in culture and 800 μl of culture media was then subjected to acetone precipitation according to Example 2 (which inactivated the virus). The resulting precipitate was resuspended in 50 μl of solution containing $ddH_2O$. 2 μl of the solubilized pellet was mixed with 2 μl of extraction buffer containing Lonzabac and DTT. 1 μl of each sample/extraction mix was loaded onto matrix precoated MALDI plates.

FIG. 7 includes a region of overlapping peaks for PR8, swine flu and LCMV in the m/z range of about 5000-7000. Diagnostic LCMV indicative peaks are visible in this m/z range. Characteristic matching peaks of the H1N1 influenza A strains can be seen in the m/z range of about 8,500 to about 10000. A new protein mass (marked with two asterisks) enables the 2009 swine flu to be distinguished from PR8.

FIG. 8 shows a MALDI-ToF mass spectrum for samples containing SARS1, SARS2 and N8 influenza pseudoviruses in which the peaks for the three samples overlap. The samples were subjected to acetone precipitation as described in Example 2. After precipitation, the samples were mixed with DTT and mass spectrometry grade pure water.

FIG. 9 shows overlaid distinct patterns of protein peaks in MALDI-ToF mass spectra enabling viral families (Arenaviridae, Coronaviridae, Orthomyxoviridae) and species thereof to be distinguished. Samples containing LCMV, Influenza A/Puerto Rico/8/1934 (H1N1 PR8), Influenza A/England/195/2009 (H1N1 Swine Flu), and SARS1, SARS2, and MERS-CoV pseudoviruses were subject to acetone precipitation as described in Example 2. After precipitation, the samples were mixed with, Lonzabac, DTT and mass spectrometry grade pure water.

FIG. 10 is a MALDI-ToF mass spectrum showing a peak at 9200 m/z which is indicative of influenza N9 neuraminidase. Control traces for SARS-CoV-2 pseudoviruses (SARS2 and DIOS) and the lentiviral vector template (VECTOR) are shown. The peak at 8550 m/z was present in all spectra and corresponds to ubiquitin.

Figure 11:
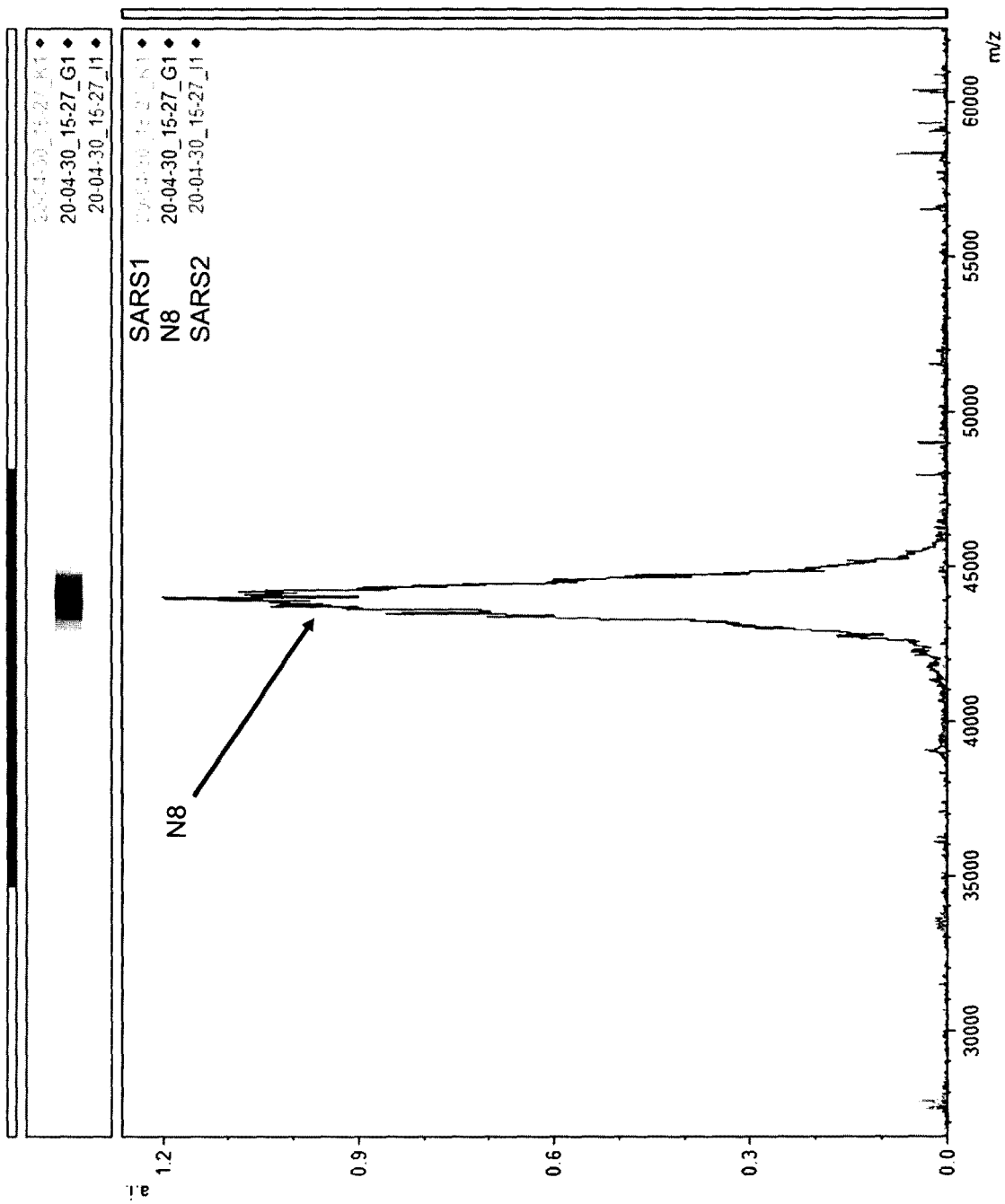
Figure 12:
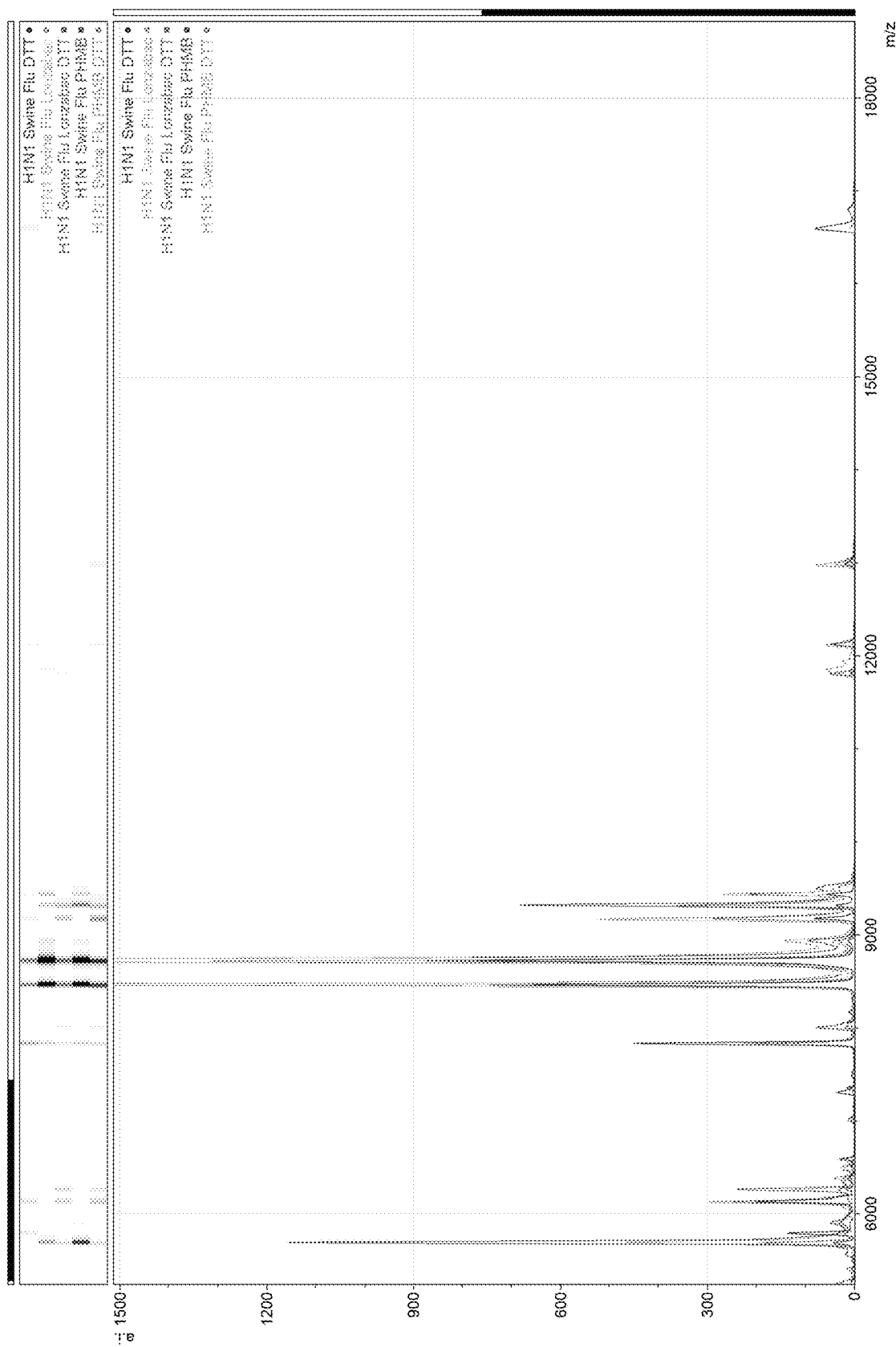
Figure 13:
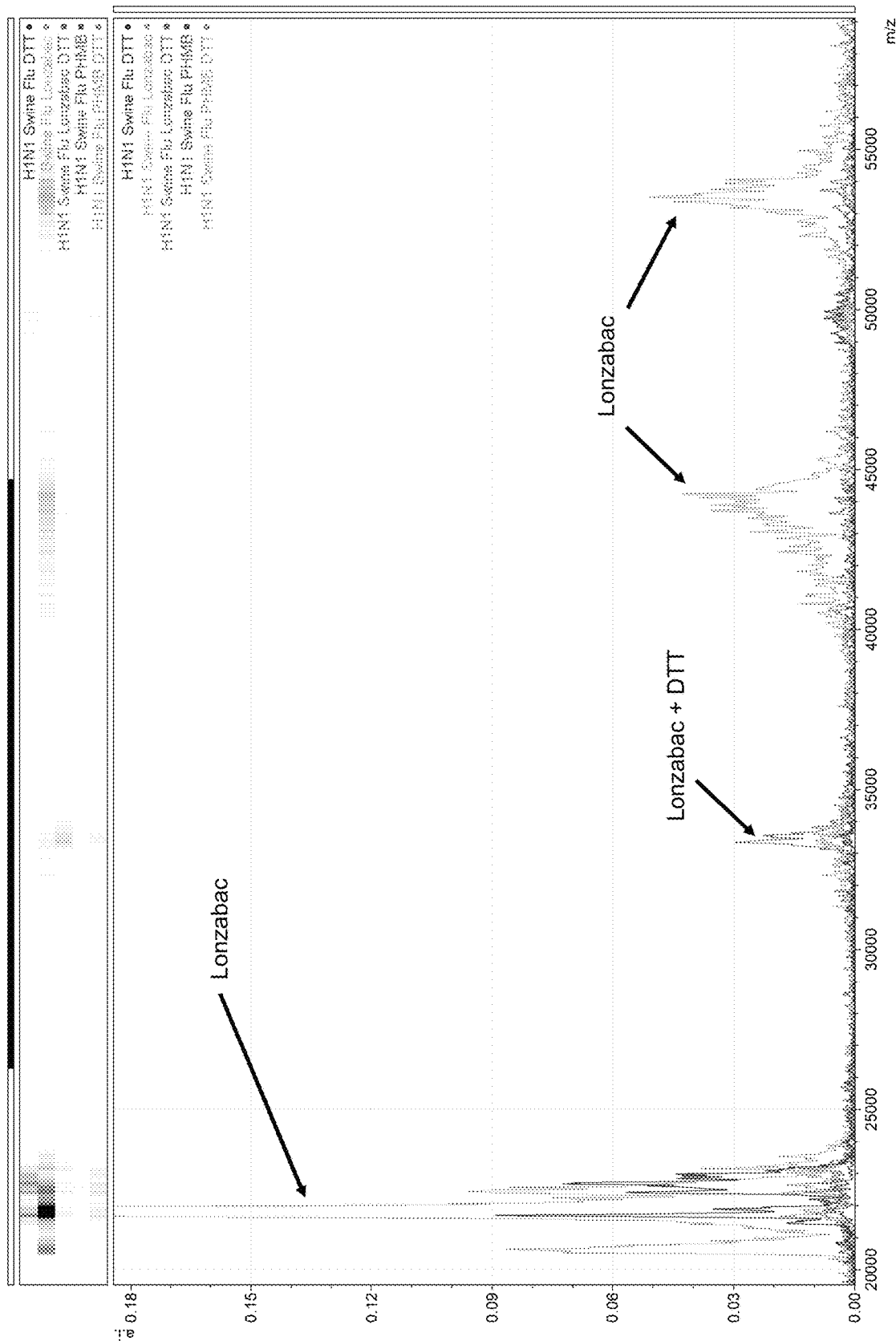
Figure 14:
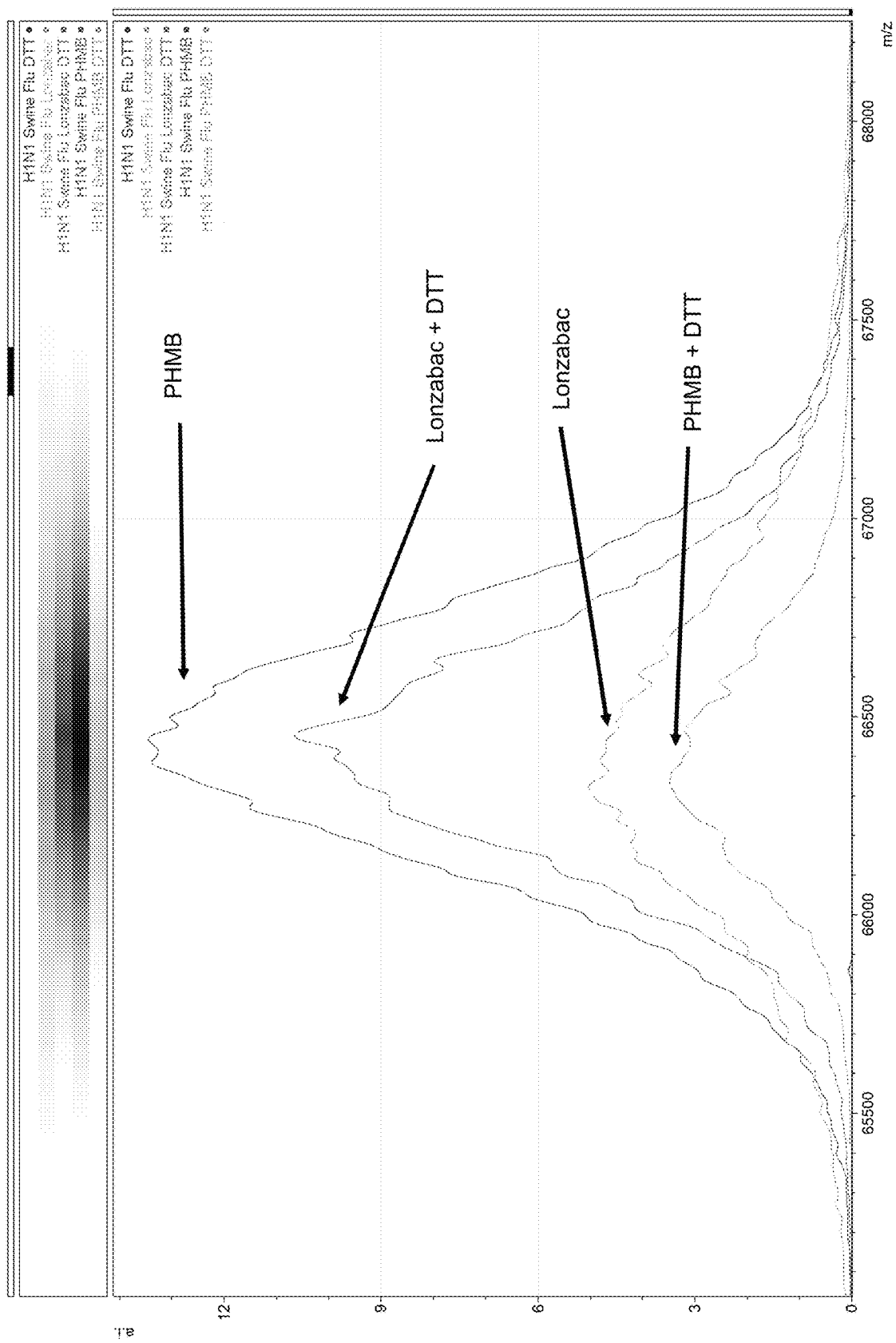

FIG. 11 is a MALDI-ToF mass spectrum showing a peak at 44000 m/z which is indicative of influenza N8 neuraminidase. The samples were subjected to acetone precipitation as described in Example 2. After precipitation, the samples were mixed with the cationic viral envelope disruptor compounds CHDG and BAC50 and the solvents acetonitrile and mass spectrometry grade pure water. The samples were not treated with a disulphide reducing agent. SARS2 and SARS1 control traces are shown.

Figure 10:
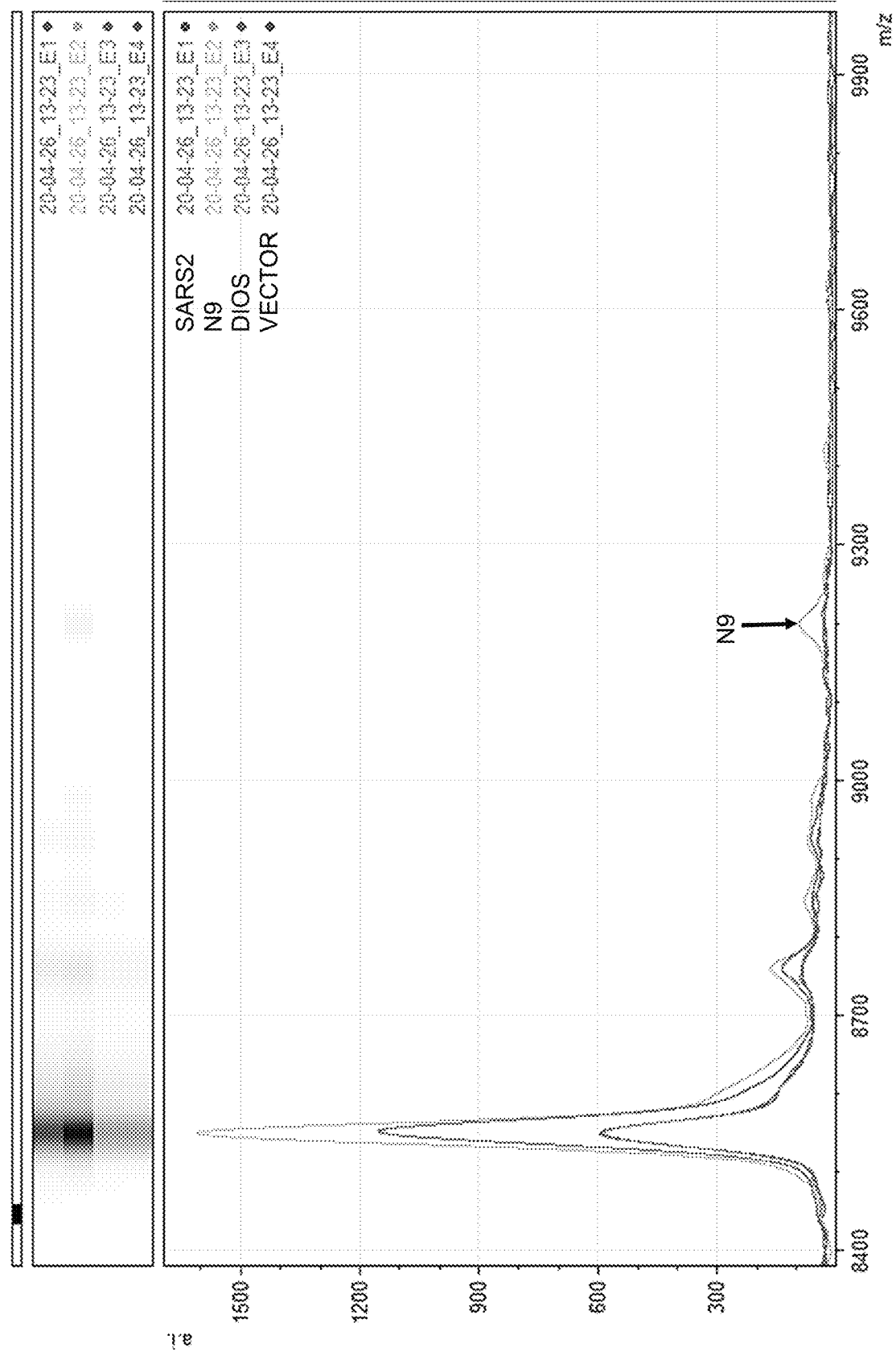

FIGS. 10 and 11 show peaks indicative of the presence of N9 and N8 influenza pseudoviruses respectively.

FIGS. 12-14 are MALDI-ToF mass spectra for samples containing H1N1 Swine Flu at three m/z ranges (FIG. 12—about 5000 to about 18000, FIG. 13 about 20000 to about 60000, FIG. 14—about 65000 to about 68000). After acetone precipitation as described in Example 2, the samples were mixed with DTT, or Lonzabac, or Lonzabac and DTT, or PHMB, or PHMB and DTT. FIG. 12 illustrates that the combination of cationic detergent with DTT enhances peak detection in the m/z range shown. FIG. 13 illustrates a preference for Lonzabac as the cationic viral envelope disruptor compound in the m/z range shown. FIG. 14 illustrates a preference for PHMB for detection of high-molecular weight protein markers.

Example 4

Specificity

Saliva samples were collected. 5 ml of each saliva sample was mixed with ice-cold (4° C.) acetone in a volume (v/v) ratio of 1:1. The mixture was then centrifuged in a refrigerated centrifuge (4° C.) at 16000 g for 30 minutes. The majority of the supernatant was removed to leave precipitate in the form of a pellet. Each pellet was then completely dissolved in 50 µl of buffer (0.001% (v/v) Lonzabac in $ddH_2O$ containing 20 mM TCEP-HCl) and the resulting solutions analysed by MALDI-ToF MS 3 Pools of blank saliva samples and 3 pools of positive saliva samples were tested in replicates of 6. In these experiments a positive result was determined as detection of S1, S2 and S2' mass spectral peaks characteristic of the SARS-CoV-2 virus. Samples were spiked with possible interfering substances as shown in the table below (Table 2). No interference was defined as spiked blank samples testing negative and spiked positive samples testing positive. Interference was defined as blank samples testing positive and positive samples testing negative.

TABLE 2

| Potential Interfering Substance | Concentration of Substance | Positive Samples Detected Pool 1 | Positive Samples Detected Pool 2 | Positive Samples Detected Pool 3 | Negative Samples Detected Pool 1 | Negative Samples Detected Pool 2 | Negative Samples Detected Pool 3 |
|---|---|---|---|---|---|---|---|
| Mouth Wash | 0.1% v/v Benzalkonium chloride and/or 0.1% Chlorohexidine | neg | neg | neg | neg | neg | neg |
| No Interfering substance (controls) | Pseudotype SARS-CoV-2 $10^3$ FU/µl | Pos | Pos | Pos | neg | neg | neg |
| Rhino Virus | Infected Individuals Gargle (conc" unknown) | Pos | Pos | Pos | neg | neg | neg |
| Human Coronavirus MERS | Pseudotypes at $10^3$ FU/µl | Pos | Pos | Pos | neg | neg | neg |
| Human Coronavirus OC43** | Pseudotypes at $10^3$ FU/µl | Pos | Pos | Pos | Pos | Pos | neg |
| Human Coronavirus 229E** | Pseudotypes at $10^3$ FU/µl | Pos | Pos | Pos | neg | neg | Pos |
| Human Coronavirus NL63 | Pseudotypes at $10^3$ FU/µl | Pos | Pos | Pos | neg | neg | neg |
| Human Coronavirus HKU1 | Pseudotypes at $10^3$ FU/µl | Pos | Pos | Pos | neg | neg | neg |
| Influenza A virus (H1N1 Swine Flu) | 1000 PFU | Pos | Pos | Pos | neg | neg | neg |
| Influenza A virus (H1N21 Puerto rico) | 1000 PFU | Pos | Pos | Pos | neg | neg | neg |

Functional infectivity assay determination of concentration.

FU = Fluorescence Unit. This is a functional transfection measure of light detection from reporter luciferase gene being expressed as a result of pseudo type virus successfully infecting target HEK293 cells in vitro. FU is determined from serial dilution of the pseudovirus samples infection of HEK293 cells in vitro.

PFU = Plaque forming Units. A biological measure of functional pathogenic virus infected Vero cells from co-culture with live virus containing samples. PFU is determined from serial dilution of the virus samples plaque formation on a Vero cell in vitro culture monolayer.

**Phylogenic related beta-coronaviruses OC43 and alpha-coronavirus 229E have similar characteristic S1, S2 and S2' mass peaks to SARS-CoV-2 which can score positive on this evaluation. An additional, non mass spectrometry, test may be required to distinguish between very similar viruses in a sample.

From the above results, it can be seen that mouthwash can interfere with the test results. Individuals providing saliva or gargle samples to be analysed by the methods of the invention should abstain from food, drink or mouthwash for at least 1 hour prior to sample collection, to avoid misleading results.

Example 5

Clinical Performance Evaluation

The FDA Emergency Use Authorization (EUA) approved Abbott SARS2 rtPCR test (Abbott RealTime SARS-CoV-2 assay) was used as comparator in this evaluation. This test requires only one of two SARS-CoV-2 genome (RdRp and Nucleocapsid) sequence primers to be positive at <40 Ct to be recorded as qualitatively positive.

The first study involved 550 samples from student athletes at Northern Illinois University, USA, taken between November and December 2020. All were nasopharyngeal swab samples tested using the Abbott rtPCR SARS-CoV-2 test. Of these 77 were rtPCR positive, 10 of which developed symptoms. This was a positivity rate of 14% of which 67 (85.7%) are defined as rtPCR "asymptomatic". Thus overall, amongst this population, 12% were rtPCR asymptomatic carriers.

One hundred and fifty two gargle-saliva samples were collect simultaneously with the nasopharyngeal swabs. A comparative evaluation study was performed to evaluate the performance of the MALDI-ToF test method of the present invention for detection of pre symptomatic and asymptomatic individuals using a Shimadzu Axima MALDI-ToF mass spectrometer. Of the 152 gargle-saliva samples analysed, 3 were pre-symptomatic rtPCR positive and 57 rtPCR positive determined asymptomatic; ninety two were rtPCR negative samples.

In this evaluation both the virus S1, S2, S2' spectral mass peaks combined threshold and that of the IgA heavy chains had to be exceeded to score positive.

TABLE 3

High threshold

| | | Abbott SARS-CoV2 rtPCR test | | |
|---|---|---|---|---|
| | | Pre-Symptomatic Positive (3) | rt PCR Asymptomatic positive (57) | rt PCR Negative (92) |
| MALDI-ToF Gargle sample test | Pre-Symptomatic Positive (3) | 3/3 | N/A | 0 |
| | Asymptomatic Positive (47) | N/A | 29/57 | 18 |
| | Negative (102) | 0 | 28 | 74/92 |
| Positive % Agreement | Pre symptomatic cases-100% | | | |
| | Asymptomatic cases 51% | | | |
| Negative % Agreement | 80% agreement on negatives | | | |

TABLE 4

Low Threshold

| | | Abbott SARS-CoV2 rtPCR test | | |
|---|---|---|---|---|
| | | Pre-Symptomatic Positive (3) | rt PCR Asymptomatic positive (57) | rt PCR Negative (92) |
| MALDI-ToF Gargle sample test | Pre-Symptomatic Positive (3) | 3/3 | N/A | 0 |
| | Asymptomatic positive (75) | N/A | 43/57 | 32 |
| | Negative (74) | 0 | 14 | 60/92 |
| Positive % Agreement | Pre symptomatic cases-100% | | | |
| | Asymptomatic cases-75% | | | |
| Negative % Agreement | 65% agreement on negatives | | | |

Figure 15:
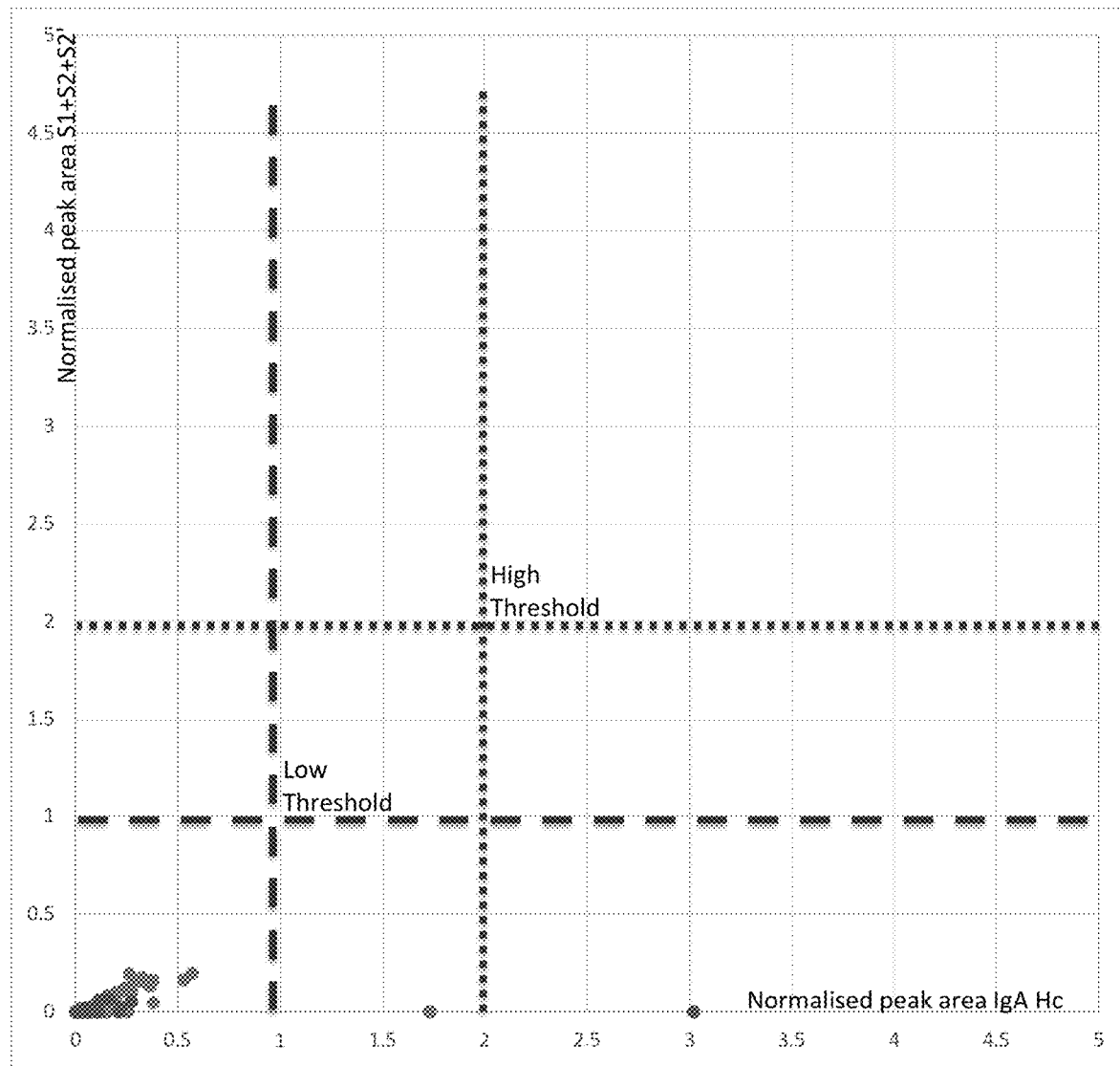

A further negative population was evaluated consisting of 150 samples from convalescent patients 3 months after recovery from confirmed (serological-positive) SARS-Cov-2 infection (27 ITU patients, 123 medical staff with mild COVID-19 symptoms). None of the 150 exceeded the threshold of positive testing in the combined S1, S2, S2' peak measure and IgA heavy chain using a Shimadzu 8020 mass spectrometer (see FIG. 15).

Figure 16:
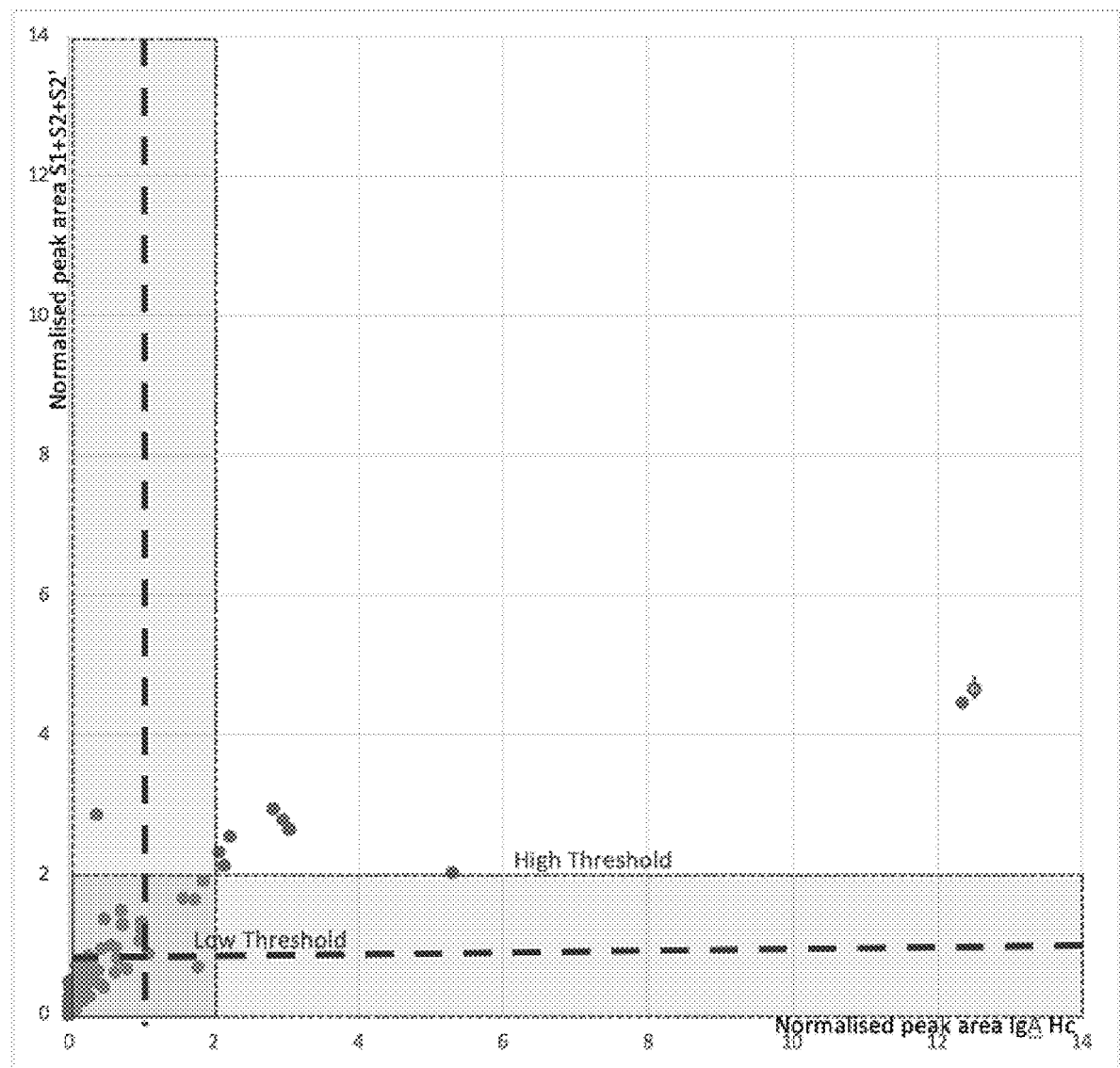

In a second field analysis, 300 members of the UK general population (volunteers from London and Bedford) gave gargle-saliva samples. Eleven scored positive on the gargle-saliva MALDI-ToF test of the present invention at a conservative threshold. When the positive thresholds were increased by a factor of two (see FIG. 16), 7 of the previous 11 scored positive. One individual (marked with ϕ in FIG. 16) reported having experienced COVID-19 symptoms requiring bed rest. The prevailing population estimates of infection amongst those not reporting symptoms for Bedfordshire and North London, UK, varied from 2.5% up to 3.5% at the time of sample collection (November 2020 to January 2021—UK Office of National Statistic (ONS)). Thus the expected rtPCR positive rate** for pre-symptomatic and asymptomatic carriers was 8 to 11. The extrapolated estimated detection of "pre-symptomatic and asymptomatic infection" therefore varied from 64% to 88% (7/[8 or 11]) to 100%-138% (11/[8 or 11]) depending on the threshold applied.

**Note: the UK government rtPCR SARS-CoV-2 testing conforms to a minimum threshold of 1 of 3 primer pairs positives for a Ct of <35 to be recorded as rtPCR positive for COVID-19 infection.

Thus, this suggests that compared to rt-PCR assays with a Ct of 35, the MALDI-ToF MS method may detect 80-100% of the PCR positive asymptomatic cases.

Example 6

Sample Stability

Storage sample stability was determined by storing saliva samples spiked with SARS-CoV2 pseudotype virus and frozen at −18 to −20° C., and subsequently analysing thawed samples at time 1 week, 2 weeks, 3 weeks and 4 weeks using a Shimadzu Axima MALDI-ToF mass spectrometer (Table 5) or a Shimadzu Kratos 8020 MALDI-ToF mass spectrometer (Table 6). If there was no change in result compared to the initial (time 0) results (positives still positive, negatives still negative) when analysed, a sample was considered stable. The results showed the samples were stable for at least 4 weeks at −20° C.

TABLE 5

| | Week 1 POS/NEG | Week 2 POS/NEG | Week 3 POS/NEG | Week 4 POS/NEG | Total POS/NEG |
|---|---|---|---|---|---|
| Positive (PCR) | 5/0 | 5/0 | 5/0 | 5/0 | 20/0 |
| Negative (PCR) | 0/5 | 0/5 | 0/5 | 0/5 | 0/20 |

TABLE 6

| | Week 1 POS/NEG | Week 2 POS/NEG | Week 3 POS/NEG | Week 4 POS/NEG | Total POS/NEG |
|---|---|---|---|---|---|
| Positive (PCR) | 5/0 | 5/0 | 5/0 | 5/0 | 20/0 |
| Negative (PCR) | 0/5 | 0/5 | 0/5 | 0/5 | 0/20 |

The above results demonstrate that samples do not need to be tested immediately after collection but can instead be frozen for analysis at a later date, which greatly increases the practicality of the test methods of the invention.

Extract stability was determined by leaving extracted, solubilised, reduced and matrix mixed/spotted samples (prepared as in Example 4) on the MALDI-ToF sample plate after time 0 analysis and rerunning the mass spectra at 12 hours, 24 hours, and 48 hours using a Shimadzu Axima MALDI-ToF mass spectrometer (Table 7) or a Shimadzu Kratos 8020 MALDI-ToF mass spectrometer (Table 8). The samples were stable for 24 hours (Table 7) or 48 hours (Table 8).

TABLE 7

| | 0 hrs POS/NEG | 12 hrs POS/NEG | 24 hrs POS/NEG | 48 hrs POS/NEG | Total POS/NEG |
|---|---|---|---|---|---|
| Positive (PCR) | 5/0 | 5/0 | 5/0 | — | 15/0 |
| Negative (PCR) | 0/5 | 0/5 | 0/5 | — | 0/15 |

TABLE 8

| | 0 hrs POS/NEG | 12 hrs POS/NEG | 24 hrs POS/NEG | 48 hrs POS/NEG | Total POS/NEG |
|---|---|---|---|---|---|
| Positive (PCR) | 10/0 | 10/0 | 10/0 | 10/0 | 50/0 |
| Negative (PCR) | 0/10 | 0/10 | 0/10 | 0/10 | 0/50 |

Example 7

Limit Of Detection (LOD) for SARS-CoV-2

The LOD is taken as the lowest concentration of virus in a sample that triggers a positive result 95% of the time. LOD was determined by diluting a saliva sample with known concentrations of virus and testing until the assay no longer detected >95% positive rate. The detection of the combined S1, S2, and S2' peaks of SARS-CoV-2 above a threshold indicated virus detection.

Shimadzu Axima MALDI-ToF mass spectrometer determination of LOD based on quantitative rtPCR determined viral copy number in an (rtPCR) saliva sample positive for SARS-CoV2 is shown in Table 9. Shimadzu 8020 mass spectrometer determined LOD based on a biological assay (PFU) of SARS-2 viral levels is shown in Table 10.

TABLE 9

| Conc. | POS/NEG | % Positive |
|---|---|---|
| 2,304 copies per ml | 10/10 | 100% |
| 1,152 copies per ml | 10/10 | 100% |
| 576 copies per ml | 10/10 | 100% |
| 288 copies per ml | 9/10 | 90% |
| 144 copies per ml | 5/10 | 50% |
| 77 copies per ml | 0/10 | 0% |

TABLE 10

| Conc. | POS/NEG | % Positive |
|---|---|---|
| 1000 PFU (200 per ml) | 10/10 | 100% |
| 750 PFU (150 per ml) | 10/10 | 100% |
| 500 PFU (100 per ml) | 5/10 | 50% |
| 10 PFU (2 per ml) | 0/10 | 0% |

In the rt PCR assay comparison (Table 9), a MALDI-ToF spectral signal was no longer detectable for a sample corresponding to 77 copies/mL as quantitated by rtPCR. A signal was seen 95% of the time at about 400 copies/ml, In biological assay of infectious SARS-CoV-2 (Wuhan isolate) (Table 10), a MALDI-ToF spectral signal was no longer detectable at 2 PFU/mL. A signal would be seen 95% of the time at about 140 PFU/mL.

The above results demonstrate the sensitivity of the methods of the invention in detecting even low viral loads.

The invention claimed is:

1. A method for analysing a biological sample for the presence of an enveloped virus, or an exosome or other extracellular vesicle, the method comprising:
    (a) treating the sample at a temperature of from −25° C. to 18° C. with a volatile organic solvent to form a precipitate comprising any virions, exosomes or other extracellular vesicles present in the sample;
    (b) separating the precipitate from the supernatant;
    (c) mixing the precipitate with:
        i. at least one cationic viral envelope/vesicle disruptor compound, or a combination of the at least one cationic viral envelope/vesicle disruptor compound and at least one disulphide reducing agent; and
        ii. at least one solvent to provide a mixture;
        wherein the at least one cationic viral envelope/vesicle disruptor compound is selected from quaternary ammonium compounds, chlorhexidine gluconate (CHDG), N-(3-aminopropyl)-N-dodecylpropane-1,3-diamine, polyhexamethylene biguanide hydrochloride (PHMB), or a combination thereof; and
    (d) subjecting the mixture to matrix assisted laser desorption ionization time of flight (MALDI-ToF) mass spectrometric analysis.

2. The method according to claim 1, wherein the sample is treated at a temperature of 2 to 10° C.

3. The method according to claim 1 wherein the volatile organic solvent is selected from acetone, a $C_{1-3}$ alcohol, ethyl acetate, butanone, chloroform or mixtures thereof.

4. The method according to claim 1, wherein the sample is treated with the volatile organic solvent at a pH of from 5 to 10.

5. The method according to claim 1 wherein the precipitate is mixed with the at least one cationic viral envelope/vesicle disruptor compound or the combination of the at least one cationic viral envelope/vesicle disruptor compound and the at least one disulphide reducing agent, and the at least one solvent in step (c) at a pH of from 5 to 10.

6. The method according to claim 1 wherein the at least one disulphide reducing agent is selected from dithiothreitol (DTT), 2-mercaptoethanol (BME), 2-mercaptoethylamine hydrochloride (2 MEA-HCl), tris(2-carboxyethyl)phosphine (TCEP) and tris(2 carboxyethyl)phosphine hydrochloride (TCEP-HCl), 1,5-diaminonaphthalene (1,5-DAN).

7. The method according to claim 1 wherein the at least one solvent in step (c) is selected from methanol, acetonitrile (ACN), water, trifluoroacetic acid (TFA), methylamine and combinations thereof.

8. The method according to claim 7, wherein the at least one solvent in step (c) comprises or is water.

9. The method according to claim 8, wherein the water is double distilled deionised water.

10. The method according to claim 1 wherein the precipitate is mixed with the at least one cationic viral envelope/vesicle disruptor compound and the at least one disulphide reducing agent.

11. The method according to claim 10, wherein the at least one disulphide reducing agent is DTT and the at least one cationic viral/vesicle envelope disruptor compound is N-(3-aminopropyl)-N-dodecylpropane-1,3-diamine.

12. The method according to claim 1, wherein the biological sample comprises the enveloped virus.

13. The method according to claim 1, wherein the biological sample comprises the exosome or other extracellular vesicle.

14. The method according to claim 1, wherein the biological sample is blood serum, blood plasma, urine, saliva, cerebrospinal fluid, washings from a swab, a gargle solution, or a bronchial or lung lavage.

15. The method according to claim 1, wherein the biological sample has been cultured in a viral receptive cell line.

16. A method of diagnosing a viral illness in a patient, the method comprising subjecting a sample from the patient to the analysis method of claim 1 to provide a mass spectrum and reviewing the mass spectrum for one of more peaks indicating the presence of a virus in the sample.

17. A method of screening a patient for a viral illness, the method comprising subjecting a sample from the patient to the analysis method of claim 1 to provide a mass spectrum and reviewing the mass spectrum for the presence or absence of one of more peaks indicative of the presence of a virus in the sample.

* * * * *